(12) United States Patent
Maruoka

(10) Patent No.: US 7,566,779 B2
(45) Date of Patent: Jul. 28, 2009

(54) OPTICALLY ACTIVE QUATERNARY AMMONIUM SALT, PROCESS FOR PRODUCING THE SAME, AND PROCESS FOR PRODUCING OPTICALLY ACTIVE α-AMINO ACID DERIVATIVE WITH THE SAME

(75) Inventor: Keiji Maruoka, Shiga (JP)

(73) Assignee: Tosoh Corporation, Yamaguchi (JP)

( * ) Notice: Subject to any disclaimer, the term of this patent is extended or adjusted under 35 U.S.C. 154(b) by 224 days.

(21) Appl. No.: 10/563,658

(22) PCT Filed: Jul. 22, 2004

(86) PCT No.: PCT/JP2004/010387

§ 371 (c)(1),
(2), (4) Date: Feb. 7, 2006

(87) PCT Pub. No.: WO2005/007622

PCT Pub. Date: Jan. 27, 2005

(65) Prior Publication Data

US 2006/0183896 A1   Aug. 17, 2006

(30) Foreign Application Priority Data

Jul. 23, 2003   (JP)   .............................. 2003-200673
Jul. 23, 2003   (JP)   .............................. 2003-200674

(51) Int. Cl.
   *C07D 223/14*   (2006.01)
(52) U.S. Cl. .............................. 540/543; 556/9; 556/437
(58) Field of Classification Search ................. 540/543; 556/437, 9
   See application file for complete search history.

(56) References Cited

U.S. PATENT DOCUMENTS 6,340,753 B1 * 1/2002 Maruoka ..................... 540/543
6,441,231 B1 * 8/2002 Maruoka ..................... 564/35

FOREIGN PATENT DOCUMENTS

JP   2002-356454      12/2002
JP   2004238362   *   8/2004

OTHER PUBLICATIONS

Ooi et al., Direct asymmetric aldol reactions of glycine Schiff base with aldehydes catalyzed by chiral quaternary ammonium salts; Angewandte Chemie, International Edition (2002), 41(23), 4542-4544.*

Ooi et al., "Design of N-Spiro $C_2$-Symmetric Chiral Quaternary Ammonium Bromides as Novel Chiral Phase-Transfer Catalysts: Synthesis and Application to Practical Asymmetric Synthesis of α-Amino Acids", Journal of the American Chemical Society, 2003, vol. 125, No. 17, pp. 5139-5151.

Maillard et al., "Chiral Perfluorous Analogues of MOP. Synthesis and Application in Catalysis", Tetrahedron: Asymmetry, 2002, vol. 13, No. 13, pp. 1449-1456, Scheme 1, 2.

Yamashita et al., "Highly Anti-Selective Asymmetric Aldol Reactions Using Chiral Zirconium Catalysts. Improvement of Activities, Structure of the Novel Zirconium Complexes, and Effect of a Small Amount of Water for the Preparation of the Catalysts", Journal of the American Chemical Society, 2002, vol. 124, No. 13, pp. 3292-3302, Scheme 2, 3.

Tian et al., "An Asymmetric Catalytic Carbon-Carbon Bond Formation In a Fluorous Biphasic System System Based on Perfluoroalkyl-BINOL", Tetrahedron Letters, 2000, vol. 41, No. 45, pp. 8813-8816, Scheme 1.

Ooi et al., "Direct Asymmetric Aldol Reactions of Glycine Schiff Base with Aldehydes Catalyzed by Chiral Quaternary Ammonium Salts", Angew Chem Int. Ed., 2002, Vol. 41, No. 23, pp. 4542-4543.

Ooi et al., "Highly Stereoselective N-Terminal Functionalization of Small Peptides by Chiral Phase-Transfer Catalysis", Angew. Chem. Int. Ed., 2003, Vol. 42, No. 5, pp. 579-582.

Ooi, et al., "Facile synthesis of L-Dopa *tert*-butyl ester by catalytic enantioselective phase-transfer alkylation", Tetrahedron Letters, 2000, vol. 41, pp. 8339-8342.

Chinchilla et al., "Asymmetric synthesis of α-amino acids using polymer-supported *Cinchona* alkaloid-derived ammonium salts as chiral phase-transfer catalysts", Tetrahedron, Asymmetry, vol. 11, 2000, pp. 3277-3281.

(Continued)

*Primary Examiner*—Daniel M Sullivan
*Assistant Examiner*—Chukwuma O Nwaonicha
(74) *Attorney, Agent, or Firm*—Nixon & Vanderhye P.C.

(57) ABSTRACT

There are provided (1) an optically active α-amino acid derivative, a stereoselectively useful intermediate for the synthesis of pharmaceutical or agrochemical products, which derivative is an optically active quaternary ammonium salt that, when used as an axially chiral spiro phase-transfer catalyst in the asymmetric alkylation of a glycine derivative, gives a high stereoselectivity toward substrates having a small molecule such as methyl iodide, or secondary alkyl halides, and a method for producing the same; and (2) a novel optically active quaternary ammonium salt that is a high performance axially chiral spiro phase-transfer catalyst used in the asymmetric alkylation of a glycine derivative, and in which each ring of the spiro-structure has the same structure that is advantageous in terms of the number of steps involved in the synthesis of the catalyst, and a method for producing the same and a method for recovering the same.

(Solving means): To achieve the objects, (1) an axially chiral spiro-ammonium salt that incorporates an alkyl- or aryl-substituted silyl group as a substituent on the aromatic ring is used as a phase-transfer catalyst in the asymmetric alkylation of a glycine derivative, and (2) an axially chiral spiro-ammonium slat that incorporates a substituent encompassing a perfluoro alkyl group is used in the asymmetric alkylation of a glycine derivative and thereafter is recovered using a fluorous solvent.

12 Claims, No Drawings

OTHER PUBLICATIONS

Thierry et al., "Solution- and Solid-Phase Approaches in Asymmetric Phase-Transfer Catalysis by Cinchona Alkaloid Derivatives", Synthesis 2001, No. 11, pp. 1742-1746.

Thierry et al., "New polymer-supported chiral phase-transfer catalysts in the asymmetric synthesis of α-amino acids: the role of a spacer", Tetrahedron, Asymmetry, vol. 12, 2001, pp. 983-986.

Danelli et al., "Immobilization of catalysts derived from *Cinchona* alkaloids on modified poly(ethylene glycol)", Tetrahedron: Ayssemetry, vol. 14, 2003, pp. 461-467.

Jew et al., "An Unusual Electronic Effect of an Aromatic-F in Phase-Transfer Catalysts Derived form *Cinchona*-Alkaloid", Organic Letters, 2002, vol. 4, No. 24, pp. 4245-4248.

Ooi et al., Design of *N*-Spiro $C_2$-Symmetric Chiral Quaternary Ammonium Bromides as Novel Chiral Phase-Transfer Catalysts: Synthesis and Application to Practical Asymmetric Synthesis of α-Amino Acids, J. Am. Chem. Soc., 2003, vol. 125, No. 17, pp. 5139-5151.

Ooi et al., "Designer Chiral Quaternary Ammonium Bifluorides as an Efficient Catalyst for Asymmetric Nitroaldol Reaction of Silyl Nitronates with Aromatic Aldehydes", J. Am. Chem. Soc., 2003, vol. 125, No. 8, pp. 2054-2055.

Nakamura et al., "Preparation of a Fluorous Chiral BINOL Derivative and Application to an Asymmetric Protonation Reaction", Tetrahedron, vol. 56, 2000, pp. 351-356.

Nakamura et al., "Recyclable fluorous chiral ligands and catalysts: asymmetric addition of diethylzinc to aromatic aldehydes catalyzed by fluorous BINOL-Ti complexes", Tetrahedron 58, 2002, pp. 3963-3969.

Tian et al., "Asymmetric catalytic carbon-carbon bond formations in a fluorous biphasic system based on perfluoroalkyl-BINOLs", Tetrahedron 58, 2002, pp. 3951-3961.

Maillard et al., "Chiral perfluorous analogues of MOP. Synthesis ans applications in catalysis", Tetrahedron, Asymmetry, vol. 13, 2002, pp. 1449-1456.

Cavazzini et al., "Palladium-catalysed asymmetric allylic alkylation in the presence of a chiral 'light fluorous' phosphine ligand", Chem. Comm. 2001, pp. 1220-1221.

Maillard et al., "Asymmetric hydrogen transfer reduction of ketones using chiral perfluorinated diimines and diamines", Tetrahedron, vol. 58, 2002, pp. 3971-3976.

Pozzi et al., "Enantioselective Catalysis in Fluorinated Media—Synthesis and Properties of Chrial Perfluoroalkylated (Salen)manganese Complexes", Eur. J. Org. Chem., 1999, pp. 1947-1955.

Cavazzini et al., "Second-generation fluorous chiral (salen) manganese complexes", Chem. Commun., 2000, pp. 2171-2172.

Cavazzini et al., "Hydrolytic kinetic resolution of terminal epoxides catalyzed by fluorous chiral Co(salen)complexes", Tetrahedron, vol. 58, 2002, 3943-3949.

Nakamura et al., "Enantioselective addition of diethylzinc to aldehydes catalyzed by fluorous β-aminoalcohols", Tetrahedron, vol. 57, 2001, pp. 5565-5571.

Kleijn et al., "Synthesis of Arylzinc Thiolates Containing Perfluoroalkyl Chains. Model Catalyst Precursors for the Enantioselective Zinc-Mediated 1,2-Addition of Dialkylzincs to Aldehydes in Fluorous Biphase Systems", Organic Letters, 1999, vol. 1, No. 6, pp. 853-855.

* cited by examiner

OPTICALLY ACTIVE QUATERNARY AMMONIUM SALT, PROCESS FOR PRODUCING THE SAME, AND PROCESS FOR PRODUCING OPTICALLY ACTIVE α-AMINO ACID DERIVATIVE WITH THE SAME

This application is the US national phase of international application PCT/JP2004/010387, filed 22 Jul. 2004, which designated the U.S. and claims priority of JP 2003-200673, filed 23 Jul. 2003, and JP 2003-200674, filed 23 Jul. 2003, the entire contents of each of which are hereby incorporated by reference.

TECHNICAL FIELD

The present invention relates to a novel axially chiral, optically active spiro-quaternary ammonium salt and a production method thereof, as well as to an intermediate for use in the production of such an ammonium salt and a production method thereof. The present invention further relates to a method for stereoselectively producing an optically active α-amino acid derivative, a useful intermediate for the synthesis of pharmaceutical or agrochemical products, by using the ammonium salt as a phase transfer catalyst.

The present invention also relates to a fluorine-containing optically active quaternary ammonium salt and a production method thereof, as well as to an intermediate useful in the production of such a salt and a production method thereof. The present invention still further relates to a method for stereoselectively producing an optically active α-amino acid derivative, a useful intermediate for the synthesis of pharmaceutical or agrochemical products, by using the fluorine-containing ammonium salt as a phase transfer catalyst, as well as to a method for recovering such a salt. More specifically, the present invention relates to a method for recovering a fluorine-containing optically active quaternary ammonium salt by using an organic solvent with all hydrogen atoms substituted with fluorine atoms (i.e., fluorous solvent).

BACKGROUND ART

As far as the background of the present invention is concerned, optically active spiro-quaternary ammonium salts (A) through (N), which are collectively represented by the following formula (15), are known:

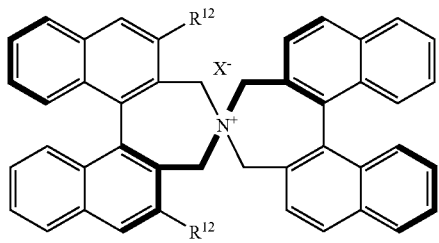

(15)

where $R^{12}$=a hydrogen atom and $X^-$=a bromide ion (Compound (A));

$R^{12}$=a phenyl group and $X^-$=a bromide ion (Compound (B));

$R^{12}$=a β-naphthyl group and $X^-$=a bromide ion (Compound (C));

$R^{12}$=a 3,4,5-trifluorophenyl group and $X^-$=a bromide ion (Compound (D));

$R^{12}$=a 3,5-bistrifluoromethylphenyl group and $X^-$=a bromide ion (Compound (E));

$R^{12}$=a 3,5-bis(3,5-bistrifluoromethylphenyl)phenyl group and $X^-$=a bromide ion (Compound (F);

$R^{12}$=a 3,5-bis-tert-butylphenyl and $X^-$=a bromide ion (Compound (G));

$R^{12}$=a 3,5-bis(3,5-bis-tert-butylphenyl)phenyl group and $X^-$=a bromide ion (Compound (H));

$R^{12}$=a β-naphthyl group and $X^-$=a thiocyanic acid ion (Compound (I));

$R^{12}$=a β-naphthyl group and $X^-$=a hydrogen sulfate ion (Compound (J));

$R^{12}$=a 3,5-bistrifluoromethylphenyl group and $X^-$=a thiocyanic acid ion (Compound (K));

$R^{12}$=a 3,5-bistrifluoromethylphenyl group and $X^-$=a hydrogen sulfate ion (Compound (L));

$R^{12}$=a 3,4,5-trifluorophenyl group and $X^-$=a thiocyanic acid ion (Compound (M)); and $R^{12}$=a 3,4,5-trifluorophenyl group and $X^-$=a hydrogen sulfate ion (Compound (N)) (See, for example, Patent Article No. 1 for Compounds (A) through (D), Non-Patent Article No. 1 for Compounds (E) and (F), Non-Patent Article No. 2 for Compounds (G) and (H), and Patent Article No. 2 for Compounds (I) through (N)).

Also, optically active spiro-quaternary ammonium salts (O) and (P), which are collectively represented by the following formula (16), are known:

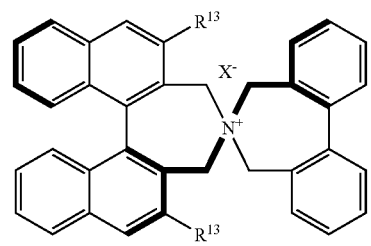

(16)

where $R^{13}$=a hydrogen atom and $X^-$=a bromide ion (Compound (O)); and $R^{13}$=a β-naphthyl group and $X^-$=a bromide ion (Compound (P)) (See Patent Article No. 3).

Furthermore, optically active spiro-quaternary ammonium salts (Q), (R), and (S), which are collectively represented by the following formula (17), are known:

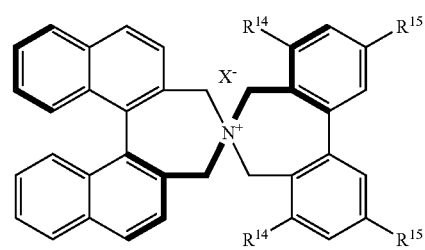

(17)

where
- $R^{14}$=a β-naphthyl group, $R^{15}$=a hydrogen atom, and $X^-$=a bromide ion (Compound(Q));
- $R^{14}$=a 3,5-diphenylphenyl, $R^{15}$=a hydrogen atom, and $X^-$=a bromide ion (Compound (R)); and
- $R^{14}$=a 3,5-diphenylphenyl group, $R^{15}$=a phenyl group, and $X^-$=a bromide ion (Compound (S)) (See Patent Article No. 3).

Still further, optically active spiro-quaternary ammonium salts (T), (U), and (V), which are collectively represented by the following formula (18), are known:

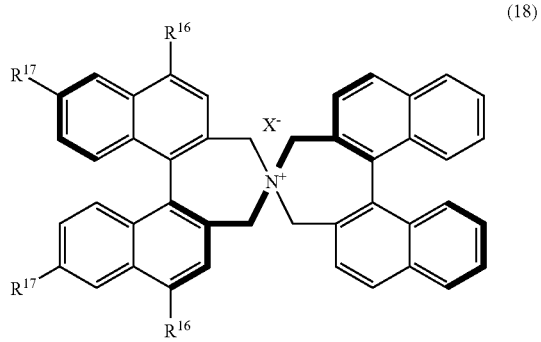

(18)

where
- $R^{16}$=$R^{17}$=a phenyl group and $X^-$=a bromide ion (Compound (T));
- $R^{16}$=a phenyl group, $R^{17}$=a hydrogen atom, and $X^-$=a bromide ion (Compound (U)); and
- $R^{16}$=$R^{17}$=a 3,5-diphenylphenyl group and $X^-$=a bromide ion (Compound (V)) (See Non-Patent Article No. 3).

Some of Compounds (A) through (V), for example Compound (D), are highly reactive and stereoselective. Nonetheless, the asymmetric structure of these compounds results in as many as 13 to 16 different steps involved in the synthesis of the catalysts when commercially available optically active 1,1-bi-2-naphthol is used as the starting material.

Still further, optically active spiro-quaternary ammonium salts (W), (X), (Y), and (Z), which are collectively represented by the following formula (19), are known:

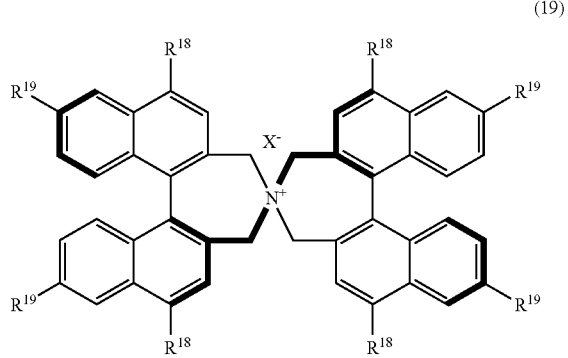

(19)

where
- $R^{18}$=$R^{19}$=a phenyl group and $X^-$=a bromide ion (Compound (W));
- $R^{18}$=a phenyl group, $R^{19}$=a hydrogen atom, and $X^-$=a bromide ion (Compound (X));
- $R^{18}$=$R^{19}$=a 3,5-diphenylphenyl group and $X^-$=a bromide ion (Compound (Y)); and
- $R^{18}$=a 3,5-diphenylphenyl group, $R^{19}$=a hydrogen atom, and $X^-$=a bromide ion (Compound (Z)) (See, for example, Non-Patent Article No. 4). Since the two binaphtyl structures in these compounds are identical to each other, the number of the steps involved in the synthesis of these catalysts is decreased to 8 to 11 steps.

In terms of catalytic performance, these catalysts show high reactivity and high selectivity of 90% or above toward certain substrates when used in the asymmetric alkylation of glycine derivatives as described in the non-patent article. However, the catalysts have been proved to show decreased reactively and selectivity toward some substrates such as ethyl iodide.

Of all the compounds represented by the following formula (1):

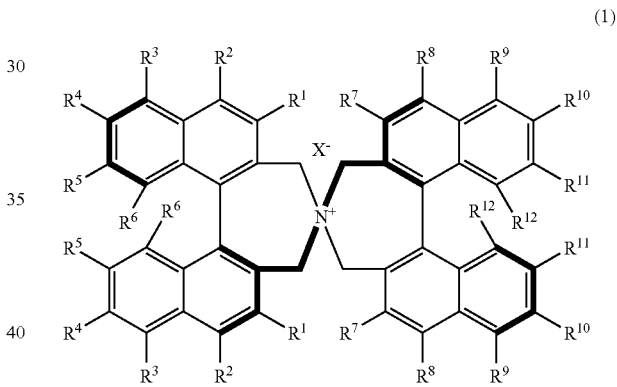

(1)

only those in which the substituents on the aromatic rings are either hydrogen or carbon atoms are known. In addition, no compounds are known that are represented by the formula (1) with silicon atoms or silicon-containing compounds directly bound to the aromatic rings.

When optically active quaternary ammonium salts are used as phase-transfer catalysts in the production of optically active α-amino acid derivatives, the catalysts may be recovered afterwards for recycle. In one technique, this is done by neutralizing the aqueous phase with an acid after separation, extracting the aqueous phase with an organic solvent, and then purifying the extract by silica gel column chromatography (Non-Patent Article No. 5). While this technique is advantageous in that the activity of the recycled catalysts is retained, the recovery of the catalyst is only 72% and the technique involves many steps. For this reason, improvement in the recovery of the catalyst is required. Also, the process for recovering catalysts must be simplified enough to be used in industrial applications.

A much simpler approach to recover catalysts involves the use of a compound represented by the following formula (20):

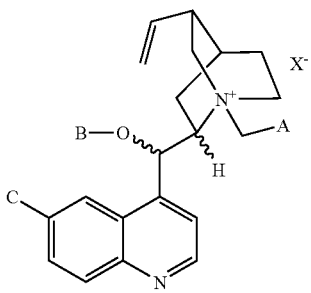

(20)

This compound comprises an ammonium salt derivative of an optically active alkaloid (e.g., quinine, quinidine, cinchonine, and cinchonidine) bound to a polymer such as polystyrene and polyethylene glycol and is suitable for use as a chiral phase-transfer catalyst in the production of optically active α-amino acid derivatives (See Non-Patent Articles 6-8 for examples in which the polymer is introduced at the position 'A', Non-Patent Article 7 for an example in which the polymer is introduced at the position 'B', and Non-Patent Article No. 9 for an example in which the polymer is introduced at the position 'C'.).

However, introduction of the polymer moiety may result in a significant decrease in the selectivity of the catalyst (See, for example, Non-Patent Article No. 9). Even many of the catalysts that retain high stereoselectivity of 90% ee or above have not been shown to retain the catalytic performance when recycled following recovery (See, for example, Non-Patent Articles 7 and 8). Although no data is presented, only one example of practically recyclable catalysts is reported. In this case, a significant reduction of the selectivity is also experienced in this example when a different substrate is used (See, for example, Non-Patent Article No. 6).

As optically active quaternary ammonium salts in which the backbone structure contains a fluorine atom as a C—F bond, alkaloid derivatives incorporating a fluorine-substituted benzyl group are known (See, for example, Non-Patent Articles 10 and 11). Also, optically active ammonium catalysts having such substituents as a 4-fluorophenyl group and a 3,4,5-trifluorophenyl group (See, for example, Non-Patent Article No. 12), a 3,5-bis(trifluoromethyl)phenyl group or a 3,5-bis{3,5-bis(trifluoromethyl)phenyl}phenyl group (See, for example, Non-Patent Article No. 13) are known as optically active quaternary ammonium salt derivatives having a chiral axis originating from binaphthyl.

However, each of these compounds contains fluorine atoms in the form of 1 to 3 fluorine substituents on the benzene ring or in the form of 1 to 8 trifluoromethyl groups: No optically active quaternary ammonium salts have been known to date that contain fluorine atoms in the form of perfluoro groups, or substituents consisting of two or more carbon atoms with all the hydrogen atoms substituted with fluorine atoms.

Different perfluoro alkyl-containing optically active asymmetric catalyst ligands are known, including axially chiral binaphthol derivatives (See, for example, Non-Patent Articles No. 14-18), optically active salen derivatives (See, for example, Non-Patent Articles No. 19-22), optically active ephedrine derivatives (See, for example, Non-Patent Article No. 23), and optically active aminothiolates (See, for example, Non-Patent Article No. 24). Each of these compounds is used in the synthesis of optically active compounds different from the compounds of the present invention. Attempts for recovery and recycle have been made for some of the compounds.

However, except for the asymmetric protonation agents used in stoichiometric amounts (Non-Patent Article 14), each compound has to be catalytically prepared through the formation of oxygen-metal bonds or complexes: No optically active organic catalysts are known that themselves serve as an asymmetric catalyst. In particular, no optically active quaternary ammonium salts are known that contain perfluoro alkyl groups consisting of two or more carbon atoms. Nor are any examples known of the use of the salts as asymmetric catalysts or as phase-transfer catalysts. No examples are known in which the phase transfer catalytic reaction is carried out in a three-phase system consisting of organic, aqueous and fluorous phases, nor are any examples described of the use of fluorous solvents to separate/purify the salts or to recover only the catalyst from the catalyst-containing mixture remaining after the reaction. No examples are known of recovering the salts to serve as catalysts in a substantially quantitative manner, nor are any examples known in which the salts are recovered in a separate phase of a fluorous solvent and the recovered salts are recycled as an asymmetric catalyst in the same reaction, and which demonstrate that the performance of the catalyst as measured by the reactivity and stereoselectivity are retained.

[Patent Article No. 1] Japanese Patent Laid-Open Publication No. 2001-48866

[Patent Article No. 2] Japanese Patent Laid-Open Publication No. 2002-173492

[Patent Article No. 3] Japanese Patent Laid-Open Publication No. 2002-326992

[Non-Patent Article No. 1] K. Maruoka et. al., Angew. Chem. Int. Ed. 2002, 41, 4542-4544

[Non-Patent Article No. 2] K. Maruoka et. al. Angew. Chem. Int. Ed. 2003, 42, 579-582

[Non-Patent Article No. 3] K. Maruoka et. al., Tetrahedron Lett. 2003, 44, 3313-3316

[Non-Patent Article No. 4] K. Maruoka et. al. Tetrahedron: Asymm. 2003, 14(12), 1599-1602

[Non-Patent Article No. 5] K. Maruoka et. al., Tetrahedron Lett. 2000, 41, 8339-8342

[Non-Patent Article No. 6] R. Chinchilla et. al., Tetrahedron: Asymm., 2000, 11, 3277-3281

[Non-Patent Article No. 7] D. Cahard et. al., Synthesis, 2001, 11, 1742-1746

[Non-Patent Article No. 8] D. Cahard et. al., Tetrahedron: Asymm., 2001, 12, 983-986

[Non-Patent Article No. 9] M. Benaglia et. al., Tetrahedron: Asymm., 2003, 14, 461-467

[Non-Patent Article No. 10] H. G. Park et. al., Org. Lett., 2002, Vol. 4, No. 24, 4245-4248

[Non-Patent Article No. 11] B. R. Cho et. al., J. Org. Chem., 1987, 52, 4752-4756

[Non-Patent Article No. 12] Keiji Maruoka et. al., J. Am. Chem. Soc., 2003, 125, 5139-5151

[Non-Patent Article No. 13] K. Maruoka et. al., J. Am. Chem. Soc., 2003, 125, 2054-2055

[Non-Patent Article No. 14] S. Takeuchi et. al., Tetrahedron, 2000, 56, 351-356

[Non-Patent Article No. 15] S. Takeuchi et. al., Tetrahedron, 2002, 58, 3963-3969

[Non-Patent Article No. 16] K. S. Chan et. al., Tetrahedron, 2002, 58, 3951-3961

[Non-Patent Article No. 17] D. Sinou et. al., Tetrahedron: Asymm., 2002, 13, 1449-1456

[Non-Patent Article No. 18] D. Sinou et. al., Chem. Commun., 2001, 1220-1221

[Non-Patent Article No. 19] D. Sinou et. al., Tetrahedron, 2002, 58, 3971-3976

[Non-Patent Article No. 20] G. Pozzi et. al., Eur. J. Org. Chem., 1999, 1947-1955

[Non-Patent Article No. 21] G. Pozzi et. al., Chem. Commun., 2000, 2171-2172

[Non-Patent Article No. 22] G. Pozzi et. al., Tetrahedron, 2002, 58, 3943-3949

[Non-Patent Article No. 23] S. Takeuchi et. al., Tetrahedron, 2001, 57, 5565-5571

[Non-Patent Article No. 24] G. v. Koten et. al., Org. Lett., 1999, Vol. 1, No. 6, 853-855

DISCLOSURE OF THE INVENTION

Problems to be Solved by the Invention

In view of the above-described state of the background art, objects of the present invention are:
1) to provide a novel axially chiral, optically active spiro-quaternary ammonium salt, that when used as a phase-transfer catalyst in the asymmetric alkylation of a glycine derivative, gives a high stereoselectivity of 90% ee or above and has a novel substituent to provide steric hindrance that allows the salt to be applied to a broader range of substrates with high selectivity, and in particular, to provide a compound in which each ring of the spiro-structure has the same structure and which is thus advantageous in terms of the number of steps involved in the synthesis of the catalyst;
2) to provide a method for producing the salts;
3) to provide an intermediate for use in the production of the salts, and a method for producing the intermediate; and
4) to provide a method for using the ammonium salts as a phase transfer catalyst and thus stereoselectively producing an optically active α-amino acid derivative suitable for use as an intermediate in the synthesis of pharmaceutical or agrochemical products.

Further objects of the present invention are:
5) to provide a novel optically active quaternary ammonium salt, that when used as a phase-transfer catalyst in the asymmetric alkylation of a glycine derivative, gives a high stereoselectivity of 90% ee or above and is readily recovered after the reaction;
6) to provide the salt that retains its catalytic performance when recycled;
7) to provide a method for readily recovering, separating, and purifying the salt at high yield after the reaction;
8) to provide a method for producing the salt;
9) to provide a method for using the salt as a phase-transfer catalyst and thus stereoselectively producing an optically active α-amino acid derivative suitable for use as an intermediate in the synthesis of pharmaceutical or agrochemical products; and
10) to recover the salt used in the reaction and ensure that high catalytic performance is retained in the recycled salt.

Means for Solving the Problems

In an effort to address the objects 1) through 4) above, the present inventor has conducted an extensive study and found a novel axially chiral, optically active ammonium salt that incorporates a novel alkyl- or aryl-substituted silyl group as a substituent on the binaphthyl aromatic ring.

In a further effort to address the objects 5) through 10) above, the present inventor has conducted extensive study and found a novel axially chiral, optically active ammonium salt that includes a perfluoro group with all hydrogen atoms substituted with fluorine atoms, and such an ammonium salt, after use as a chiral phase-transfer catalyst, can be extracted for recycle with a fluorous solvent that has all hydrogen atoms substituted with fluorine atoms. It is these findings that led to the present invention.

Accordingly, the present invention concerns an optically active quaternary ammonium salt, a method for producing the ammonium salt, a method for producing an optically active α-amino acid derivative using the ammonium salt, and a method for recovering the ammonium salt, as follows.

[1] An optically active quaternary ammonium salt, represented by the following formula (1a):

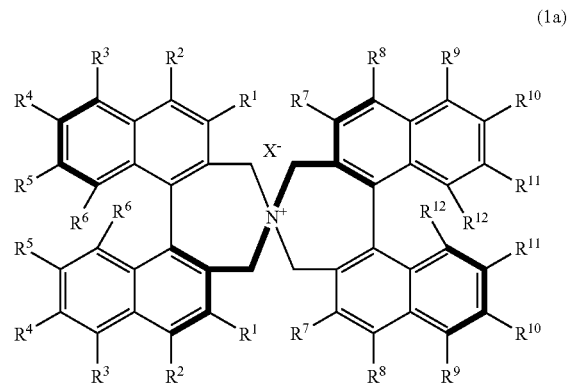

(1a)

[wherein $R^1$, $R^2$, $R^3$, $R^4$, $R^5$, $R^6$, $R^7$, $R^8$, $R^9$, $R^{10}$, $R^{11}$, and $R^{12}$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, $R^6$, $R^7$, $R^8$, $R^9$, $R^{10}$, $R^{11}$, and $R^{12}$ is a substituent represented by the following formula (2a):

(2a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.);

X⁻ is a fluorine ion, a chloride ion, a bromide ion, an iodide ion, a p-toluenesulfonic acid ion, a hydroxide ion, a thiocyanate ion, a hydrogen sulfate ion, a perchloric acid ion, or a hexafluorophosphoric acid ion; and the two binaphthyl moieties each have a chiral axis so that the absolute configurations of the two binaphthyl moieties are (R, R) or (S, S)].

[2] The optically active quaternary ammonium salt according to [1] above, wherein $R^1$ and $R^7$, $R^3$ and $R^9$, $R^4$ and $R^{10}$, $R^5$ and $R^{11}$, and $R^6$ and $R^{12}$ in the formula (1a) are in each case identical to one another; $R^2$ and $R^8$ are identical to one another and are each represented by the formula (2a); and X⁻ is a fluorine ion, a chloride ion, a bromide ion, an iodide ion, a p-toluenesulfonic acid ion, or a hydroxide ion.

[3] The optically active quaternary ammonium salt according to [1] above, wherein $R^1$, $R^3$, $R^5$, $R^6$, $R^7$, $R^9$, $R^{11}$, and $R^{12}$ in the formula (1a) are each independently a hydrogen atom; $R^2$, $R^4$, $R^8$, and $R^{10}$ are identical to one another and are each represented by the formula (2a); and X⁻ is a chloride ion, a bromide ion, an iodide ion, or a p-toluenesulfonic acid ion.

[4] The optically active quaternary ammonium salt according to [1] above, wherein in the formula (1a), $R^1$ and $R^7$, $R^3$ and $R^9$, $R^4$ and $R^{10}$, $R^5$ and $R^{11}$, and $R^6$ and $R^{12}$ are in each case identical to one another, $R^2$ and $R^8$ are identical to one another and are each represented by the formula (2a), and X⁻ is a bromide ion; and $R^{13}$, $R^{14}$ and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

[5] An optically active quaternary ammonium salt represented by the following formula (1b):

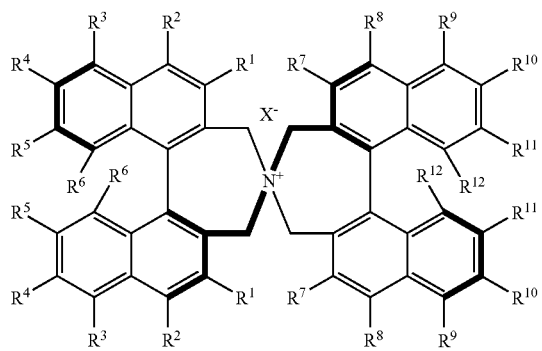

[wherein $R^1$, $R^2$, $R^3$, $R^4$, $R^5$, $R^6$, $R^7$, $R^8$, $R^9$, $R^{10}$, $R^{11}$, and $R^{12}$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, $R^6$, $R^7$, $R^8$, $R^9$, $R^{10}$, $R^{11}$, and $R^{12}$ is a substituent represented by the following formula (2b):

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms. n is an integer from 0 to 4.), and/or by the following formula (2c):

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.);

X⁻ is a fluoride ion, a chloride ion, a bromide ion, an iodide ion, a p-toluenesulfonic acid ion, a hydroxide ion, a thiocyanate ion, a hydrogen sulfate ion, a perchloric acid ion, or a hexafluorophosphoric acid ion; and the two binaphthyl moieties each have a chiral axis so that the absolute configurations of the two binaphthyl moieties are (R, R) or (S, S)].

[6] The optically active quaternary ammonium salt according to [5] above, wherein $R^1$ and $R^7$, $R^3$ and $R^9$, $R^4$ and $R^{10}$, $R^5$ and $R^{11}$, and $R^6$ and $R^{12}$ in the formula (1b) are in each case identical to one another; $R^2$ and $R^8$ are identical to one another and are each represented by the formula (2a); and X⁻ is a fluorine ion, a chloride ion, a bromide ion, an iodide ion, a p-toluenesulfonic acid ion, a thiocyanate ion, a hydrogen sulfate ion, or a hydroxide ion.

[7] The optically active quaternary ammonium salt according to [5] above, wherein $R^1$, $R^3$, $R^5$, $R^6$, $R^7$, $R^9$, $R^{11}$, and $R^{12}$ in the formula (1b) are each independently a hydrogen atom; $R^2$, $R^4$, $R^8$, and $R^{10}$ are identical to one another and are each represented by the formula (2c); and X⁻ is a chloride ion, a bromide ion, an iodide ion, or a p-toluenesulfonic acid ion.

[8] The optically active quaternary ammonium salt according to [5] above, wherein in the formula (1b), $R^1$ and $R^7$, $R^3$ and $R^9$, $R^4$ and $R^{10}$, $R^5$ and $R^{11}$, and $R^6$ and $R^{12}$ are in each case identical to one another, and $X^-$ is a bromide ion; and in the formula (2c), n is 2, $R^{13}$ and $R^{14}$ are each a methyl group, and Pf is an n-octyl group having all the hydrogen atoms substituted with fluorine atoms.

[9] An optically active binaphthyl compound represented by the following formula (3a):

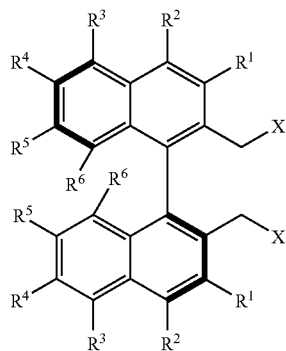

(3a)

[wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

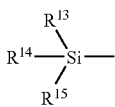

(2a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); X is a chlorine atom, a bromine atom, an iodine atom, or a p-toluenesulfonyloxy group; and the binaphthyl moiety has a chiral axis so that the absolute configuration of the binaphthyl moiety is (R) or (S)].

[10] The optically active binaphthyl compound according to [9] above, wherein $R^1$, $R^3$, $R^5$, and $R^6$ in the formula (3a) are each independently a hydrogen atom; and $R^2$ and $R^4$ are identical to one another and are each represented by the formula (2a).

[11] The optically active binaphthyl compound according to [9] above, wherein in the formula (3a), $R^1$, $R^3$, $R^5$, and $R^6$ are each independently a hydrogen atom, $R^2$ and $R^4$ are identical to one another and are each represented by the formula (2a), and X is a bromine atom; and $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

[12] An optically active binaphthyl compound represented by the following formula (3b):

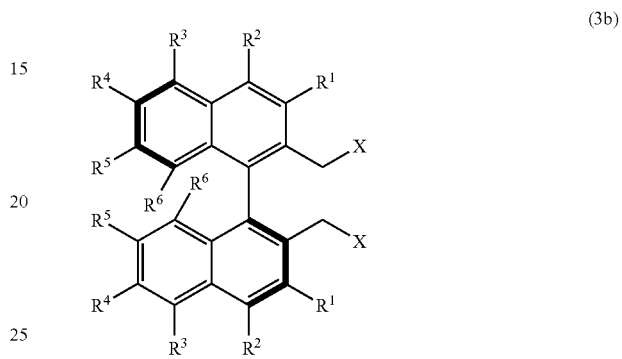

(3b)

[wherein $R^1$, $R^2$, $R^3$, $R^4$, $R^5$ and $R^6$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, and $R^6$ is a substituent represented by the following formula (2b):

$$Pf(CH_2)_n— \quad (2b)$$

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

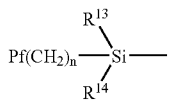
(2c)

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.);

X is a chlorine atom, a bromine atom, an iodine atom, or a p-toluenesulfonyloxy group; and the binaphthyl moiety has a chiral axis so that the absolute configuration of the binaphthyl moiety is (R) or (S)].

[13] The optically active binaphthyl compound according to [12] above, wherein $R^1$, $R^3$, $R^5$, and $R^6$ in the formula (3b) are each independently a hydrogen atom; and $R^2$ and $R^4$ are identical to one another and are each represented by the formula (2c).

[14] The optically active binaphthyl compound according to [12] above, wherein in the formula (3b), $R^1$, $R^3$, $R^5$, and $R^6$ are each independently a hydrogen atom, $R^2$ and $R^4$ are identical to one another and are each represented by the formula (2c), and X is a bromine atom; and in the formula (2c), n is 2, $R^{13}$ and $R^{14}$ are each a methyl group, and Pf is an n-octyl group having all the hydrogen atoms substituted with fluorine atoms.

[15] A method for producing the optically active quaternary ammonium salt according to any of [1] to [8] above represented by the formula (1a) or (1b) in which $X^-$ is a chloride ion, a bromide ion, an iodide ion, or a p-toluenesulfonic acid ion, characterized in that the optically active binaphthyl compound above represented by the formula (3a) or (3b) is reacted with ammonia.

[16] An optically active binaphthyl dihydroxyl compound represented by the following formula (4a):

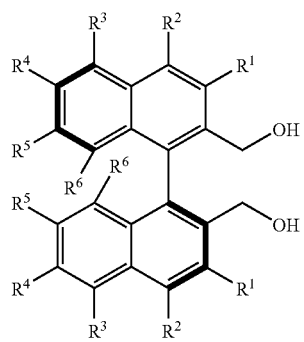
(4a)

[wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

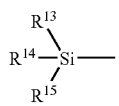
(2a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); and the binaphthyl moiety has a chiral axis so that the absolute configuration of the binaphthyl moiety is (R) or (S)].

[17] The optically active binaphthyl dihydroxyl compound according to [16] above, wherein $R^1$, $R^3$, $R^5$, and $R^6$ in the formula (4a) are each independently a hydrogen atom; and $R^2$ and $R^4$ are identical to one another and are each represented by the formula (2a).

[18] The optically active binaphthyl dihydroxyl compound according to [16] above, wherein in the formula (4a), $R^1$, $R^3$, $R^5$, and $R^6$ are each independently a hydrogen atom, and $R^2$ and $R^4$ are identical to one another and are each represented by the formula (2a); and $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

[19] An optically active binaphthyl dihydroxyl compound represented by the following formula (4b):

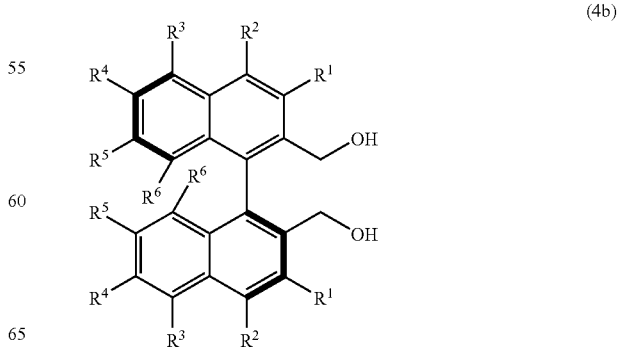
(4b)

[wherein $R^1$, $R^2$, $R^3$, $R^4$, $R^5$, and $R^6$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, and $R^6$ is a substituent represented by the following formula (2b):

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.); and the binaphthyl moiety has a chiral axis so that the absolute configuration of the binaphthyl moiety is (R) or (S)].

[20] The optically active binaphthyl dihydroxyl compound according to [19] above, wherein $R^1$, $R^3$, $R^5$, and $R^6$ in the formula (4b) are each independently a hydrogen atom; and $R^2$ and $R^4$ are identical to one another and are each represented by the formula (2c).

[21] The optically active binaphthyl dihydroxyl compound according to [19] claim 10 above, wherein in the formula (4b), $R^1$, $R^3$, $R^5$, and $R^6$ are each independently a hydrogen atom, and $R^2$ and $R^4$ are identical to one another and are each represented by the formula (2c); and in the formula (2c), n is 2, $R^{13}$ and $R^{14}$ are each a methyl group, and Pf is an n-octyl group having all the hydrogen atoms substituted with fluorine atoms.

[22] A method for producing the optically active binaphthyl compound of the formula (3a) or (3b) according to any of [9] to [14], characterized in that the optically active binaphthyl dihydroxyl compound of the formula (4a) or (4b) according to any of [16] to [21] is reacted with a halogen source or p-toluenesulfonyl chloride.

[23] An optically active binaphthyl diester compound represented by the following formula (5a):

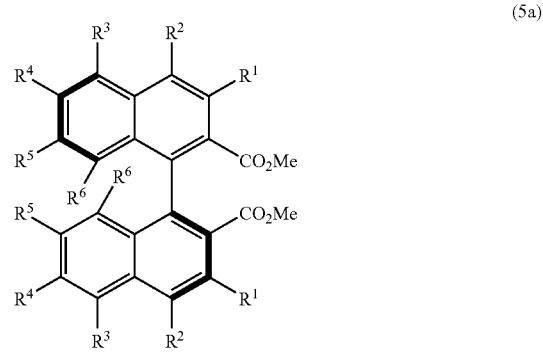

[wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); and the binaphthyl moiety has a chiral axis so that the absolute configuration of the binaphthyl moiety is (R) or (S)].

[24] The optically active binaphthyl diester compound according to [23] above, wherein $R^1$, $R^3$, $R^5$, and $R^6$ in the formula (3a) are each independently a hydrogen atom; and R² and R⁴ are identical to one another and are each represented by the formula (2a).

[25] The optically active binaphthyl diester compound according to [23] above, wherein in the formula (5a), R¹, R³, R⁵, and R⁶ are each independently a hydrogen atom, R² and R⁴ are identical to one another and are each represented by the formula (2a), and R¹³, R¹⁴, and R¹⁵ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

[26] An optically active binaphthyl diester compound represented by the following formula (5b):

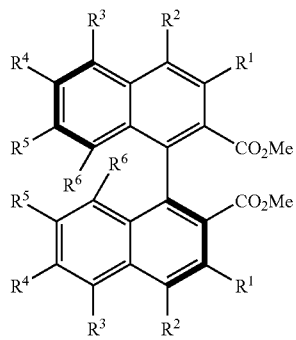

[wherein R¹, R², R³, R⁴, R⁵, and R⁶ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of R¹, R², R³, R⁴, R⁵, and R⁶ is a substituent represented by the following formula (2b):

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

$$Pf(CH_2)_n - \underset{R^{14}}{\overset{R^{13}}{Si}} - \qquad (2c)$$

(wherein Pf and n are as defined in the formula (2b) above, R¹³ and R¹⁴ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.); and the binaphthyl moiety has a chiral axis so that the absolute configuration of the binaphthyl moiety is (R) or (S)].

[27] The optically active binaphthyl diester compound according to [26] above, wherein R¹, R³, R⁵, and R⁶ in the formula (5b) are each independently a hydrogen atom; and R² and R⁴ are identical to one another and are each represented by the formula (2c).

[28] The optically active binaphthyl diester compound according to [26] above, wherein in the formula (5b), R¹, R³, R⁵, and R⁶ are each independently a hydrogen atom, and R² and R⁴ are identical to one another and are each represented by the formula (2c); and in the formula (2c), n is 2, R¹³ and R¹⁴ are each a methyl group, and Pf is an n-octyl group having all the hydrogen atoms substituted with fluorine atoms.

[29] A method for producing the compound according to any of [16] to [21] above represented by the formula (4a) or (4b), characterized in that the optically active binaphthyl diester compound according to any of [23] to [28] above represented by the formula (5a) or (5b) is reacted with a hydrogen anion.

[30] An optically active binaphthyl compound represented by the following formula (6a):

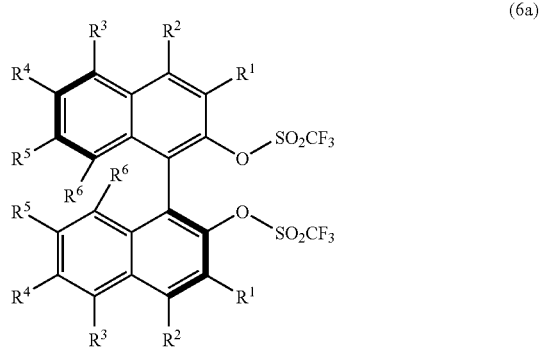

[wherein R¹, R², R³, R⁴, R⁵, and R⁶ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

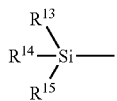

(2a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); and the binaphthyl moiety has a chiral axis so that the absolute configuration of the binaphthyl moiety is (R) or (S)].

[31] The optically active binaphthyl compound according to [30] above, wherein $R^1$, $R^3$, $R^5$, and $R^6$ in the formula (6a) are each independently a hydrogen atom; and $R^2$ and $R^4$ are identical to one another and are each represented by the formula (2a).

[32] The optically active binaphthyl compound according to [30] above, wherein in the formula (6a), $R^1$, $R^3$, $R^5$, and $R^6$ are each independently a hydrogen atom, and $R^2$ and $R^4$ are identical to one another and are each represented by the formula (2a); and $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

[33] An optically active binaphthyl compound represented by the following formula (6b):

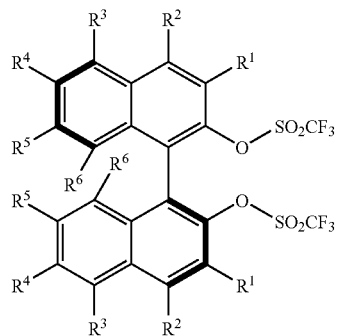

(6b)

[wherein $R^1$, $R^2$, $R^3$, $R^4$, $R^5$, and $R^6$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, and $R^6$ is a substituent represented by the following formula (2b):

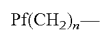

Pf(CH$_2$)$_n$— (2b)

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

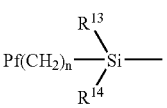

(2c)

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl-group having 1 to 18 carbon atoms, an aryl group having 5 to 20 carbon atoms, an aralkyl group having 5 to 25 carbon atoms, or a heteroaralkyl group having 5 to 25 carbon atoms.); and the binaphthyl moiety has a chiral axis so that the absolute configuration of the binaphthyl moiety is (R) or (S)].

[34] The optically active binaphthyl compound according to [33] above, wherein $R^1$, $R^3$, $R^5$, and $R^6$ in the formula (6b) are each independently a hydrogen atom; and $R^2$ and $R^4$ are identical to one another and are each represented by the formula (2c).

[35] The optically active binaphthyl compound according to [33] above, wherein in the formula (6b), $R^1$, $R^3$, $R^5$, and $R^6$ are each independently a hydrogen atom, and $R^2$ and $R^4$ are identical to one another and are each represented by the formula (2c); and in the formula (2c), n is 2, $R^{13}$ and $R^{14}$ are each a methyl group, and Pf is an n-octyl group having all the hydrogen atoms substituted with fluorine atoms.

[36] A method for producing the optically active binaphthyl diester compound of the formula (5a) or (5b) according to any of [23] to [28], characterized in that the optically active binaphthyl compound of the formula (6a) or (6b) according to any of [30] to [35] is reacted with carbon monoxide and methanol in the presence of a palladium catalyst and an organic base.

[37] An optically active binaphthol compound represented by the following formula (7a):

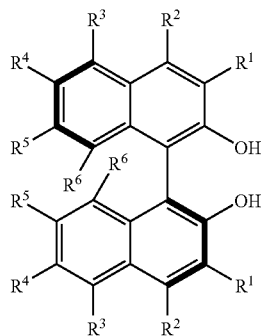
(7a)

[wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

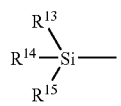
(2a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); and the binaphthyl moiety has a chiral axis so that the absolute configuration of the binaphthyl moiety is (R) or (S)].

[38] The optically active binaphthol compound according to [37] above, wherein $R^1$, $R^3$, $R^5$, and $R^6$ in the formula (7a) are each independently a hydrogen atom; and $R^2$ and $R^4$ are identical to one another and are each represented by the formula (2a).

[39] The optically active binaphthol compound according to [37] above, wherein in the formula (7a), $R^1$, $R^3$, $R^5$, and $R^6$ are each independently a hydrogen atom, $R^2$ and $R^4$ are identical to one another and are each represented by the formula (2a), and $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

[40] An optically active binaphthol compound represented by the following formula (7b):

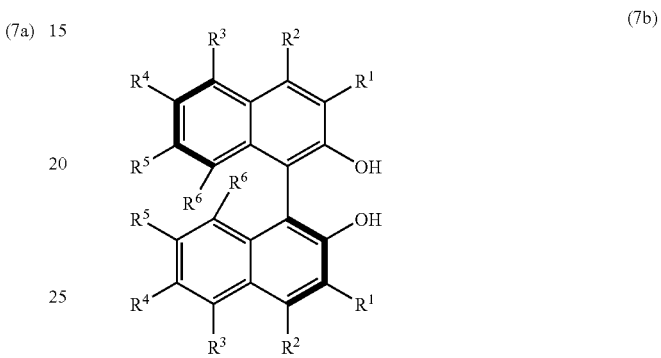
(7b)

[wherein $R^1$, $R^2$, $R^3$, $R^4$, $R^5$, and $R^6$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, and $R^6$ is a substituent represented by the following formula (2b):

$$Pf(CH_2)_n—\qquad(2b)$$

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

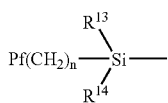

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.); and the binaphthyl moiety has a chiral axis so that the absolute configuration of the binaphthyl moiety is (R) or (S)].

[41] The optically active binaphthol compound according to [40] above, wherein $R^1$, $R^3$, $R^5$, and $R^6$ in the formula (7b) are each independently a hydrogen atom; and $R^2$ and $R^4$ are identical to one another and are each represented by the formula (2c).

[42] The optically active binaphthol compound according to [40] above, wherein in the formula (7b), $R^1$, $R^3$, $R^5$, and $R^6$ are each independently a hydrogen atom, and $R^2$ and $R^4$ are identical to one another and are each represented by the formula (2c); and in the formula (2c), n is 2, $R^{13}$ and $R^{14}$ are each a methyl group, and Pf is an n-octyl group having all the hydrogen atoms substituted with fluorine atoms.

[43] A method for producing the optically active binaphthyl compound according to any of [30] to [35] above represented by the formula (6a) or (6b), characterized in that the optically active binaphthol compound according to any of [37] to [42] above represented by the formula (7a) or (7b) is reacted with a triflating agent.

[44] An optically active binaphthyl bis-methoxymethyl ether compound represented by the following formula (8a):

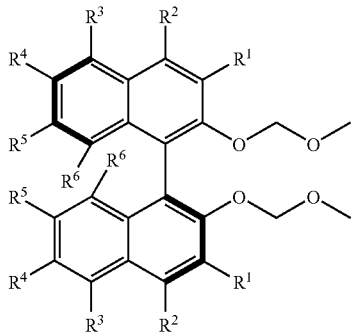

[wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); and the binaphthyl moiety has a chiral axis so that the absolute configuration of the binaphthyl moiety is (R) or (S)].

[45] The optically active binaphthyl bis-methoxymethyl ether compound according to [44] above, wherein $R^1$, $R^3$, $R^5$, and $R^6$ in the formula (8a) are each independently a hydrogen atom; and $R^2$ and $R^4$ are identical to one another and are each represented by the formula (2a)

[46] The optically active binaphthyl bis-methoxymethyl ether compound according to [44] above, wherein in the formula (8a), $R^1$, $R^3$, $R^5$, and $R^6$ are each independently a hydrogen atom, $R^2$ and $R^4$ are identical to one another and are each represented by the formula (2a), and $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

[47] An optically active binaphthyl bis-methoxymethyl ether compound represented by the following formula (8b):

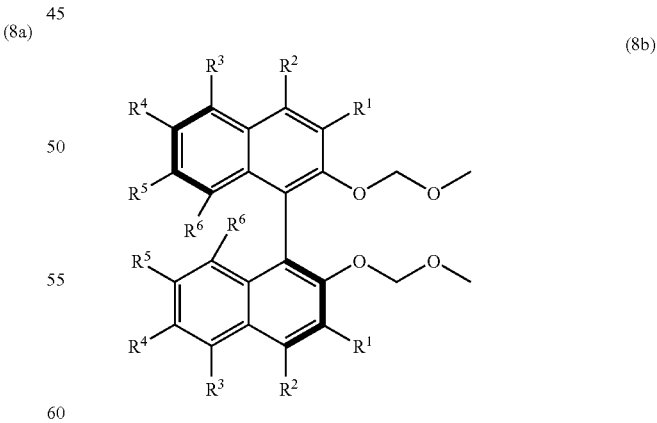

[wherein $R^1$, $R^2$, $R^3$, $R^4$, $R^5$, and $R^6$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, and $R^6$ is a substituent represented by the following formula (2b):

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

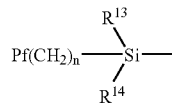

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.); and the binaphthyl moiety has a chiral axis so that the absolute configuration of the binaphthyl moiety is (R) or (S)].

[48] The optically active binaphthyl bis-methoxymethyl ether compound according to [47] above, wherein $R^1$, $R^3$, $R^5$, and $R^6$ in the formula (8b) are each independently a hydrogen atom; and $R^2$ and $R^4$ are identical to one another and are each represented by the formula (2c).

[49] The optically active binaphthyl bis-methoxymethyl ether compound according to [47] above, wherein in the formula (8b), $R^1$, $R^3$, $R^5$, and $R^6$ are each independently a hydrogen atom, and $R^2$ and $R^4$ are identical to one another and are each represented by the formula (2c); and in the formula (2c), n is 2, $R^{13}$ and $R^{14}$ are each a methyl group, and Pf is an n-octyl group having all the hydrogen atoms substituted with fluorine atoms.

[50] A method for producing the optically active binaphthol compound according to any of [37] to [42] above represented by the formula (7a) or (7b), characterized in that the optically active binaphthyl bis-methoxymethyl ether compound according to any of [44] to [49] above represented by the formula (8a) or (8b) is reacted with an acid.

[51] An optically active binaphthyl bis-methoxymethyl ether compound represented by the following formula (9a):

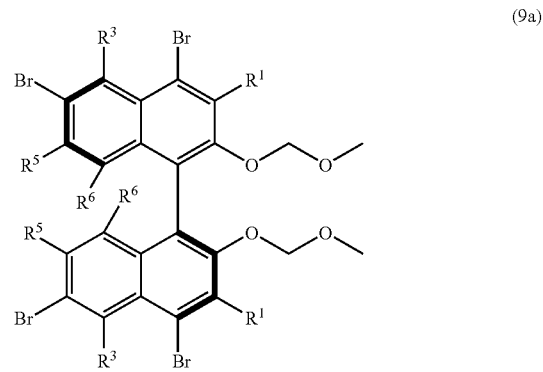

[wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); and the binaphthyl moiety has a chiral axis so that the absolute configuration of the binaphthyl moiety is (R) or (S)].

[52] The optically active binaphthyl bis-methoxymethyl ether compound according to [51] above, wherein $R^1$, $R^3$, $R^5$, and $R^6$ in the formula (9a) are each independently a hydrogen atom.

[53] A method for producing the optically active binaphthyl bis-methoxymethyl ether compound according to any of [44] to [46] above represented by the formula (8a), comprising reacting with an alkyl lithium the optically active binaphthyl bis-methoxymethyl ether compound according to any of [51] or [52] above represented by the formula (9a), and subsequently reacting with the reaction product a silyl chloride represented by the following formula (10a):

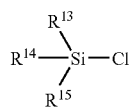

(10a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms).

[54] A method for producing the optically active binaphthyl bis-methoxymethyl ether compound represented by the formula (8b.), comprising reacting with an alkyl lithium an optically active binaphthyl bis-methoxymethyl ether compound represented by the following formula (9b):

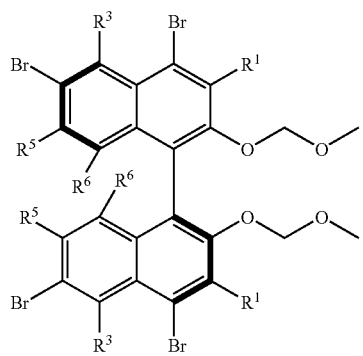

(9b)

[wherein $R^1$, $R^2$, $R^3$, $R^4$, $R^5$, and $R^6$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, and $R^6$ is a substituent represented by the following formula (2b):

$Pf(CH_2)_n$—

(2b)

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

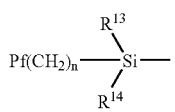

(2c)

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, a heteroaralkyl group having 5 to 25 carbon atoms, or a substituent represented by the formula (2b)); and the binaphthyl moiety has a chiral axis so that the absolute configuration of the binaphthyl moiety is (R) or (S).], and subsequently reacting with the reaction product a compound represented by the following formula (10c):

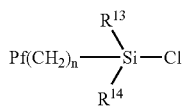

(10c)

[wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, a heteroaralkyl group that has 5 to 25 carbon atoms and has all the hydrogen atoms substituted with fluorine atoms, n is an integer from 0 to 4, and $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, a heteroaralkyl group having 5 to 25 carbon atoms, or a substituent represented by the formula (2b).]

[55] A method for producing the optically active binaphthyl bis-methoxymethyl ether compound according to any of [51] or [52] above represented by the formula (9a), comprising forming a binaphthoxide from an optically active binaphthol compound represented by the following formula (11a) in the presence of an acid-capturing agent or by treatment with a base:

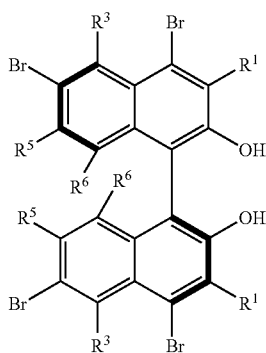

(11a)

[wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, and $R^6$ is a substituent represented by the following formula (2a):

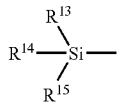

(2a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms); and the binaphthyl moiety has a chiral axis so that the absolute configuration of the binaphthyl moiety is (R) or (S).], and subsequently reacting the binaphthoxide with chloromethyl ether.

[56] A method for stereoselectively producing a compound represented by the following formula (14):

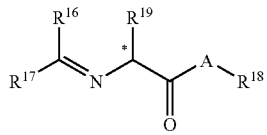

(14)

[wherein $R^{16}$, $R^{17}$, $R^{18}$, $R^{19}$, and A are as defined above, and the chiral carbon indicated by an asterisk '*' has an absolute configuration of (R) or (S)], comprising reacting, in a two-phase solution, a Schiff base of a glycine ester or an amide represented by the following formula (12):

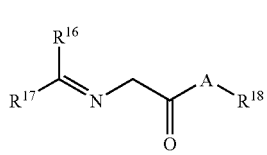

(12)

[wherein $R^{16}$ and $R^{17}$ are each independently a hydrogen atom or an aryl group that has 5 to 10 carbon atoms and may or may not be substituted with halogen, with the proviso that $R^{16}$ and $R^{17}$ are not a hydrogen atom at the same time;

$R^{18}$ is a straight, branched or cyclic alkyl group having 1 to 6 carbon atoms; and A is an oxygen atom or a nitrogen atom having a single hydrogen atom bound thereto] with an alkyl halide represented by the following formula (13):

$$R^{19}-Y \qquad (13)$$

[wherein $R^{19}$ is a straight, branched or cyclic alkyl group having 1 to 10 carbon atoms, a straight, branched or cyclic alkenyl group having 3 to 10 carbon atoms, a straight, branched or cyclic alkynyl group having 3 to 10 carbon atoms, or an aralkyl group that has 5 to 25 carbon atoms and may or may not have its nucleus substituted with 1 to 15 halogen atoms; and Y is a chlorine atom, a bromine atom, or an iodine atom] in the presence of an optically active quaternary ammonium salt according to [1] to [8] above represented by the formula (1a) or (1b) and an inorganic base.

[57] The method according to [56] above, wherein the reaction is carried out in a three-phase solution comprising an organic solvent with hydrogen atoms substituted with fluorine atoms, an organic solvent, and water.

[58] A method for recovering an optically active quaternary ammonium salt, characterized in that an organic solvent, water, a mixed solvent of an organic solvent and water, and/or an organic solvent with hydrogen atoms substituted with fluorine atoms are/is used to separate the optically active quaternary ammonium salt according to any of claims 5 to 8 represented by the formula (1b) from a product containing the ammonium salt.

[59] A method for recovering the optically active quaternary ammonium salt according to any of [5] to [8] above represented by the formula (1b), characterized in that, following the production of the compound of the formula (14) by the method according to [56] above, which is carried out in the presence of the optically active quaternary ammonium salt of the formula (1b), the ammonium salt is separated from the reaction mixture containing the optically active quaternary ammonium salt by using an organic solvent, water, a mixed solvent of an organic solvent and water, and/or an organic solvent with hydrogen atoms substituted with fluorine atoms.

[60] The method according to [59] above, wherein hexane with its hydrogen atoms substituted with fluorine atoms is used as the fluorine-substituted organic solvent.

ADVANTAGE OF THE INVENTION

The axially chiral, optically active spiro-quaternary ammonium salts of the formula (1a) provided in accordance with the present invention can give a high stereoselectivity of 90% ee or above when used as a phase-transfer catalyst in the asymmetric alkylation of a glycine derivative, and can be applied to a broader range of substrates with high selectivity. The ammonium salts are advantageous since fewer steps are involved in the synthesis of the catalysts. Furthermore, when used as a phase-transfer catalyst, the ammonium salts allow the stereoselective production of optically active α-amino acid derivatives, useful intermediates in the synthesis of pharmaceutical or agrochemical products. Because of these advantages, the present invention is of significant importance in industrial applications.

The fluorine-containing optically active quaternary ammonium salts of the formula (1b) provided in accordance with the present invention are spiro compounds with a chiral axis and can serve as effective phase-transfer catalysts when used in the asymmetric alkylation of glycine derivatives. Furthermore, the optically active quaternary ammonium salts can be readily produced, recovered, and purified, and can retain high catalytic activity after they are recycled. Furthermore, when used as a phase-transfer catalyst, the optically active quaternary ammonium salts allow the stereoselective production of optically active α-amino acid derivatives, useful intermediates in the synthesis of pharmaceutical or agrochemical products. These advantages further add to the industrial importance of the present invention.

BEST MODE FOR CARRYING OUT THE INVENTION

The present invention will now be described in detail.

While the optically active quaternary ammonium salt of the present invention shown by the formula (1a) may be any of the compounds defined above, it preferably is a compound in which $R^1$ and $R^7$, $R^3$ and $R^9$, $R^4$ and $R^{10}$, $R^5$ and $R^{11}$, and $R^6$ and $R^{12}$ are in each case identical to one another, $R^2$ and $R^8$ are identical to one another and are each represented by the formula (2a), and $X^-$ is a fluoride ion, a chloride ion, a bromide ion, an iodide ion, a p-toluenesulfonic acid ion, or a hydroxide ion. Of such compounds, particularly preferred are those in which $R^1$, $R^3$, $R^5$, $R^6$, $R^7$, $R^9$, $R^{11}$, and $R^{12}$ are each a hydrogen atom, $R^2$, $R^4$, $R^8$, and $R^{10}$ are identical to one another and are each represented by the formula (2a), and $X^-$ is a chloride ion, a bromide ion, an iodide ion, or a p-toluenesulfonic acid ion. Of these, even more preferred are those in which $X^-$ in the formula (1a) is a bromide ion, and $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

Examples of the compound shown by the formula (1a) include, but are not limited to, spiro-bis[{(R)-1,1'-bi-{4,6-bis(trimethylsilyl)naphthyl}}-2,2'-dimethyl]ammonium bromide, spiro-bis[{(R)-1,1'-bi-{4,6-bis(triethylsilyl)naphthyl}}-2,2'-dimethyl]ammonium bromide, spiro-bis[{(R)-1,1'-bi-{4,6-bis(tripropylsilyl)naphthyl}}-2,2'-dimethyl]ammonium bromide, spiro-bis[{(R)-1,1'-bi-{4,6-bis(triisopropylsilyl)naphthyl}}-2,2'-dimethyl]ammonium bromide, spiro-bis[{(R)-1,1'-bi-{4,6-bis(tributylsilyl)naphthyl}}-2,2'-dimethyl]ammonium bromide, spiro-bis[{(R)-1,1'-bi-{4,6-bis(triphenylsilyl)naphthyl}}-2,2'-dimethyl]ammonium bromide, spiro-bis[{(R)-1,1'-bi-{4,6-bis(dimethyloctylsilyl)naphthyl}}2,2.'-dimethyl]ammonium bromide, spiro-bis[{(R)-1,1'-bi-{4,6-bis(tert-butyldimethylsilyl)naphthyl}}-2,2'-dimethyl]ammonium bromide, spiro-bis[{(R)-1,1'-bi-{4,6-bis(dimethylphenylsilyl)naphthyl}}-2,2'-dimethyl]ammonium bromide, spiro-bis[{(R)-1,1'-bi-{4,6-bis(tert-butyldiphenylsilyl)naphthyl}}-2,2'-dimethyl]ammonium bromide, spiro-bis[{(R)-1,1'-bi-{4,6-bis(trimethylsilyl)naphthyl}}-2,2'-dimethyl]ammonium iodide, spiro-bis[{(R)-1,1'-bi-{4,6-bis(trimethylsilyl)naphthyl}}-2,2'-dimethyl]ammonium chloride, spiro-bis[{(R)-1,1'-bi-{4,6-bis(trimethylsilyl)naphthyl}}-2,2'-dimethyl]ammonium fluoride and spiro-bis[{(R)-1,1'-bi-{4,6-bis(trimethylsilyl)naphthyl}}-2,2'-dimethyl]ammonium hydroxide, and the corresponding (S)-forms as enantiomers.

While the optically active quaternary ammonium salt of the present invention shown by the formula (1b) may be any of the compounds defined above, it preferably is a compound in which $R^1$ and $R^7$, $R^3$ and $R^9$, $R^4$ and $R^{10}$, $R^5$ and $R^{11}$, and $R^6$ and $R^{12}$ are in each case identical to one another, $R^2$ and $R^8$ are identical to one another and are each represented by the formula (2c), and $X^-$ is a fluoride ion, a chloride ion, a bromide ion, an iodide ion, a p-toluenesulfonic acid ion, or a hydroxide ion. Of such compounds, more preferred are those in which $R^1$, $R^3$, $R^5$, $R^6$, $R^7$, $R^9$, $R^{11}$, and $R^{12}$ in the formula (1b) are each a hydrogen atom, $R^2$, $R^4$, $R^8$, and $R^{10}$ are identical to one another and are each represented by the formula (2c), and $X^-$ is a chloride ion, a bromide ion, an iodide ion, or a p-toluenesulfonic acid ion. Of these, most preferred are those in which $X^-$ in the formula (1b) is a bromide ion, and in the formula (2c), n is 2, $R^{13}$ and $R^{14}$ are each a methyl group, and Pf is an n-octyl group having all the hydrogen atoms substituted with fluorine atoms.

Examples of the compound shown by the formula (1b) include, but are not limited to, spiro-bis{(R)-1,1'-bi-[4-(2-perfluorooctylethyl)dimethylsilyl]naphthyl-2,2'-dimethyl}ammonium bromide, spiro-bis{(R)-1,1'-bi-[6-(2-perfluorooctylethyl)dimethylsilyl]naphthyl-2,2'-dimethyl}ammonium bromide, spiro-bis{(R)-1,1'-bi-[4-(2-perfluorooctylethyl)dimethylsilyl-6-(2-perfluorooctyl)ethyl]naphthyl-2,2'-dimethyl}ammonium bromide, spiro-bis{(R)-1,1'-bi-[4,6-bis((2-perfluorooctylethyl)dimethylsilyl)]naphthyl-2,2'-dimethyl]ammonium bromide, spiro-bis{(R)-1,1'-bi-[4,6-bis(-tris(2-perfluorooctylethyl)silyl)]naphthyl-2,2'-dimethyl}ammonium bromide, spiro-bis{(R)-1,1'-bi-[4,6-bis((2-perfluorooctylethyl)dimethylsilyl)]naphthyl-2,2'-dimethyl}ammonium fluoride, spiro-bis{(R)-1,1'-bi-[4,6-bis((2-perfluorooctylethyl)dimethylsilyl)]naphthyl-2,2'-dimethyl}ammonium chloride, spiro-bis{(R)-1,1'-bi-[4,6-bis((2-perfluorooctylethyl)dimethylsilyl)]naphthyl-2,2'-dimethyl}ammonium iodide, spiro-bis{(R)-1,1'-bi-[4,6-bis((2-perfluorooctylethyl)dimethylsilyl)]naphthyl-2,2'-dimethyl}ammonium hydroxide, and spiro-bis{(R)-1,1'-bi-[4,6-bis((2-perfluorooctylethyl)

dimethylsilyl)]naphthyl-2,2'-dimethyl}ammonium-4-methylbenzene sulfonate, and the corresponding (S)-forms as enantiomers.

While the optically active binaphthyl compound of the present invention shown by the formula (3a) may be any of the compounds defined above, it preferably is a compound in which $R^1$, $R^3$, $R^5$, and $R^6$ are each a hydrogen atom, and $R^2$ and $R^4$ are identical to one another and are each represented by the formula (2a). Of these, particularly preferred are those in which $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group. Of these compounds, those in which X is a chlorine atom, a bromine atom, an iodine atom, or p-toluenesulfonyloxy group are preferred, with ones in which X is a bromine atom being particularly preferred.

Examples of the optically active binaphthyl compound of the present invention shown by the formula (3a) include, but are not limited to, (R)-1,1'-bi-{2-bromomethyl-4,6-bis(trimethylsilyl)}naphthyl, (R)-1,1'-bi-{2-bromomethyl-4,6-bis(triethylsilyl))naphthyl, (R)-1,1'-bi-{2-bromomethyl-4,6-bis(tripropylsilyl)}naphthyl, (R)-1,1'-bi-{2-bromomethyl-4,6-bis(triisopropylsilyl)}naphthyl, (R)-1,1'-bi-{2-bromomethyl-4,6-bis(tributylsilyl)}naphthyl, (R)-1,1'-bi-{2-bromomethyl-4,6-bis(triphenylsilyl)}naphthyl, (R)-1,1'-bi-12-bromomethyl-4,6-bis(dimethyloctylsilyl)}naphthyl, (R)-1,1'-bi-{2-bromomethyl-4,6-bis(tert-butyldimethylsilyl)}naphthyl, (R)-1,1'-bi-{2-bromomethyl-4,6-bis(dimethylphenylsilyl)}naphthyl, (R)-1,1'-bi-{2-bromomethyl-4,6-bis(tert-butyldiphenylsilyl)}naphthyl, (R) -1,1'-bi-{2-chloromethyl-4,6-bis(trimethylsilyl)}naphthyl, (R)-1,1'-bi-{2-chloromethyl-4,6-bis(trimethylsilyl)}naphthyl and (R)-1,1'-bi-{2-iodomethyl-4,6-bis(trimethylsilyl)}naphthyl, and the corresponding (S)-forms as enantiomers.

The optically active binaphthyl compound of the present invention shown by the formula (3b) is preferably such that $R^1$, $R^3$, $R^5$, and $R^6$ are each a hydrogen atom, and $R^2$ and $R^4$ are identical to one another and are each represented by the formula (2c). Of such compounds, particularly preferred are those in which X in the formula (3b) is a bromine atom, and in the formula (2c), n is 2, $R^{13}$ and $R^{14}$ are each a methyl group, and Pf is an n-octyl group having all the hydrogen atoms substituted with fluorine atoms.

Examples of the optically active binaphtyl compound of the present invention shown by the formula (3b) include, but are not limited to, (R)-1,1'-bi-{2-bromomethyl-4-(2-perfluorooctylethyl)dimethylsilyl}naphthyl, (R)-1,1'-bi-{2-bromomethyl-6-(2-perfluorooctylethyl)dimethylsilyl}naphthyl, (R)-1,1'-bi-{2-bromomethyl-4-(2-perfluorooctylethyl)dimethylsilyl-6-(2-perfluorooctyl)ethyl}naphthyl, (R)-1,1'-bi-{2-bromomethyl-4,6-bis((2-perfluorooctylethyl)dimethylsilyl)}naphthyl, (R)-1,1'-bi-{2-bromomethyl-4,6-bis[-tris(2-perfluorooctylethyl)silyl]}naphthyl, (R)-1,1'-bi-{2-chloromethyl-4,6-bis[(2-perfluorooctylethyl)dimethylsilyl]}naphthyl, (R)-1,1'-bi-{2-iodomethyl-4,6-bis((2-perfluorooctylethyl)dimethylsilyl)}naphthyl and (R)-1,1'-bi-{2-(4-methylbenzenesulfonyloxy)methyl-4,6-bis[(2-perfluorooctylethyl)dimethylsilyl]}naphthyl, and the corresponding (S)-forms as enantiomers.

The compound of the present invention represented by the formula (1a) or (1b) can be obtained by reacting the optically active binaphthyl compound of the formula (3a) or (3b) with ammonia. The ammonia used may be a 10 wt % to saturated aqueous ammonia and preferably a 20 to 28 wt % aqueous ammonia. Water or an organic solvent inert to the reaction may be added as a solvent. The reaction is preferably carried out in a sealed condition to avoid loss of ammonia. The amount of ammonia used is typically 1 to 8 equivalents, and preferably 2 to 5 equivalents, relative to the substrate used. The reaction is typically carried out at a temperature of 5° C. to 30° C. and at a substrate concentration of 5 to 20 wt %, and is carried out over a time period of typically 5 to 72 hours, and preferably 10 to 36 hours. In this manner, the desired ammonium salt can be obtained in high yield.

While the optically active binaphthyl dihydroxy compound of the present invention shown by the formula (4a) may be any of the compounds defined above, it preferably is a compound in which $R^1$, $R^3$, $R^5$, and $R^6$ are each a hydrogen atom, and $R^2$ and $R^4$ are identical to one another and are each represented by the formula (2a). Of these, particularly preferred are those in which $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

Examples of the optically active binaphthyl dihydroxy compound of the present invention shown by the formula (4a) include, but are not limited to, (R)-1,1'-bi-{4,6-bis(trimethylsilyl)-2-hydroxymethyl}naphthyl, (R)-1,1'-bi-{4,6-bis(triethylsilyl)-2-hydroxymethyl}naphthyl, (R)-1,1'-bi-{4,6-bis(tripropylsilyl)-2-hydroxymethyl}naphthyl, (R)-1,1'-bi-{4,6-bis(triisopropylsilyl-2-hydroxymethyl)naphthyl, (R)-1,1'-bi-{4,6-bis(tributylsilyl)-2-hydroxymethyl}naphthyl, (R)-1,1'-bi-{4,6-bis(triphenylsilyl)-2-hydroxymethyl}naphthyl, (R)-1,1'-bi-{4,6-bis(dimethyloctylsilyl)-2-hydroxymethyl}naphthyl, (R)-1,1'-bi-{4,6-bis(tert-butyldimethylsilyl)-2-hydroxymethyl)naphthyl, (R)-1,1'-bi-{4,6-bis(dimethylphenylsilyl)-2-hydroxymethyl}naphthyl and (R)-1,1'-bi-{4,6-bis(tert-butyldiphenylsilyl)-2-hydroxymethyl}naphthyl, and the corresponding (S)-forms as enantiomers.

The optically active binaphthyl dihydroxy compound of the present invention shown by the formula (4b) is preferably such that $R^1$, $R^3$, $R^5$, and $R^6$ are each a hydrogen atom, and $R^2$ and $R^4$ are identical to one another and are each represented by the formula (2c). Of such compounds, most preferred are those in which in the formula (2c), $R^{13}$ and $R^{14}$ are each a methyl group, Pf is an n-octyl group having all the hydrogen atoms substituted with fluorine atoms, and n is 2.

Examples of the optically active binaphthyl dihydroxy compound of the present invention shown by the formula (5) include (R)-1,1'-bi-{2-hydroxymethyl-4-(2-perfluorooctylethyl)dimethylsilyl}naphthyl, (R)-1,1'-bi-{2-hydroxymethyl-6-(2-perfluorooctylethyl)dimethylsilyl}naphthyl, (R)-1,1'-bi-{2-hydroxymethyl-4-(2-perfluorooctylethyl)dimethylsilyl-6-(2-perfluorooctyl)ethyl}naphthyl, (R)-1,1'-bi-{2-hydroxymethyl-4,6-bis[(2-perfluorooctylethyl)dimethylsilyl]}naphthyl and (R)-1,1'-bi-{2-hydroxymethyl-4,6-bis[-tris(2-perfluorooctylethyl)silyl]}naphthyl, and the corresponding (S)-forms as enantiomers.

The optically active binaphthyl compound of the present invention represented by the formula (3a) or (3b) can be obtained as follows: For example, when it is desired to produce a halogenated product, the optically active binaphthyl dihydroxy compound of the formula (4a) or (4b) is reacted with triphenylphosphine, and carbon tetrabromide or carbon tetrachloride in a proper solvent such as tetrahydrofuran. The reaction is carried out at a substrate concentration of typically 5 to 20 wt % and at a temperature of typically −10° C. to 50° C., and preferably 10° C. to 30° C., and is carried out over a time period of typically 10 minutes to 10 hours, and preferably 1 hour to 5 hours. In this manner, the desired dihalogenated product can be obtained in high yield. When it is desired to produce a sulfonyloxy product, the optically active binaphthyl dihydroxy compound (4a) or (4b) is reacted with p-toluenesulfonyl chloride in a proper solvent such as dichloromethane and in the presence of an acid-capturing agent such as triethylamine. The reaction is carried out at a substrate concentration of typically 5 to 20 wt % and at a temperature of typically −40° C. to 20° C., and preferably −10° C. to 10° C., and is carried out over a time period of typically 10 minutes to 10 hours, and preferably 1 hour to 5 hours. In this manner, the desired sulfonyloxy product can be obtained in high yield.

While the optically active binaphthyl diester compound of the present invention shown by the formula (5a) may be any of the compounds defined above, it preferably is a compound in which $R^1$, $R^3$, $R^5$, and $R^6$ are each a hydrogen atom, and $R^2$ and $R^4$ are identical to one another and are each represented by the formula (2a). Of these, particularly preferred are those in which $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

Examples of the optically active binaphthyl diester compound of the present invention shown by the formula (5a) include (R)-1,1'-bi-{4,6-bis(trimethylsilyl)-2-methoxycarbonyl}naphthyl, (R)-1,1'-bi-{4,6-bis(triethylsilyl)-2-methoxycarbonyl}naphthyl, (R)-1,1'-bi-{4,6-bis(tripropylsilyl)-2-methoxycarbonyl}naphthyl, (R)-1,1'-bi-{4,6-bis(triisopropylsilyl)-2-methoxycarbonyl}naphthyl, (R)-1,1'-bi-{4,6-bis(tributylsilyl)-2-methoxycarbonyl}naphthyl, (R)-1,1'-bi-{4,6-bis(triphenylsilyl)-2-methoxycarbonyl}naphthyl, (R)-1,1'-bi-{4,6-bis(dimethyloctylsilyl)-2-methoxycarbonyl}naphthyl, (R)-1,1'-bi-{4,6-bis(tert-butyldimethylsilyl)-2-methoxycarbonyl}naphthyl, (R)-1,1'-bi-{4,6-bis(dimethylphenylsilyl)-2-methoxycarbonyl}naphthyl and (R)-1,1'-bi-{4,6-bis(tert-butyldiphenylsilyl)-2-methoxycarbonyl}naphthyl, and the corresponding (S)-forms as enantiomers.

The optically active binaphthyl diester compound of the present invention shown by the formula (5b) is preferably such that $R^1$, $R^3$, $R^5$, and $R^6$ are each a hydrogen atom, and $R^2$ and $R^4$ are identical to one another and are each represented by the formula (2c). Of such compounds, particularly preferred are those in which in the formula (2c), $R^{13}$ and $R^{14}$ are each a methyl group, Pf is an n-octyl group having all the hydrogen atoms substituted with fluorine atoms, and n is 2.

Examples of the optically active binaphthyl diester compound of the present invention shown by the formula (5b) include, but are not limited to, (R)-1,1'-bi-{2-methoxycarbonyl-4-(2-perfluorooctylethyl)dimethylsilyl}naphthyl, (R)-1,1'-bi-{2-methoxycarbonyl-6-(2-perfluorooctylethyl)dimethylsilyl}naphthyl, (R)-1,1'-bi-{2-methoxycarbonyl-4-(2-perfluorooctylethyl)dimethylsilyl-6-(2-perfluorooctyl)ethyl}naphthyl, (R)-1,1'-bi-{2-methoxycarbonyl-4,6-bis[(2-perfluorooctylethyl)dimethylsilyl]}naphthyl and (R)-1,1'-bi-{2-methoxycarbonyl-4,6-bis[-tris(2-perfluorooctylethyl)silyl]}naphthyl, and the corresponding (S)-forms as enantiomers.

The optically active binaphthyl dihydroxy compound of the present invention represented by the formula (4a) or (4b) can be obtained, for example, by reacting the optically active binaphthyl diester compound of the formula (5a) or (5b) with a hydrogen anion such as $LiAlH_4$ in a proper solvent such as tetrahydrofuran. The reaction is carried out at a substrate concentration of typically 5 to 30 wt % and at a temperature of typically −20° C. to 30° C., and preferably −10° C. to 10° C., and is carried out over a time period of typically 10 minutes to 5 hours, and preferably 20 minutes to 2 hours. In this manner, the desired dihydroxyl methyl product can be obtained in high yield.

While the optically active binaphthyl compound of the present invention shown by the formula (6a) may be any of the compounds defined above, it preferably is a compound in which $R^1$, $R^3$, $R^5$, and $R^6$ are each a hydrogen atom, and $R^2$ and $R^4$ are identical to one another and are each represented by the formula (2a). Of these, particularly preferred are those in which $R^{13}$, $R^{14}$, and $R^{15}$ in the formula (2a) are each independently a substituent, selected from the group consisting of a methyl group, an ethyl group, an n-propyl group, an isopropyl group, an n-butyl group, an isobutyl group, a sec-butyl group, a tert-butyl group, an n-octyl group, and a phenyl group.

Examples of the optically active binaphthyl compound of the present invention shown by the formula (6a) include, but are not limited to, (R)-1,1'-bi-{4,6-bis(trimethylsilyl)-2-trifluoromethanesulfonyl}naphthyl, (R)-1,1'-bi-{4,6-bis(triethylsilyl)-2-trifluoromethanesulfonyl}naphthyl, (R)-1,1'-bi-{4,6-bis(tripropylsilyl)-2-trifluoromethanesulfonyl}naphthyl, (R)-1,1'-bi-{4,6-bis(triisopropylsilyl)-2-trifluoromethanesulfonyl}naphthyl, (R)-1,1'-bi-{4,6-bis(tributylsilyl)-2-trifluoromethanesulfonyl}naphthyl, (R)-1,1'-bi-{4,6-bis(triphenylsilyl)-2-trifluoromethanesulfonyl}naphthyl, (R)-1,1'-bi-{4,6-bis(dimethyloctylsilyl)-2-trifluoromethanesulfonyl}naphthyl, (R)-1,1'-bi-{4,6-bis(tert-butyldimethylsilyl)-2-trifluoromethanesulfonyl}naphthyl, (R)-1,1'-bi-{4,6-bis(dimethylphenylsilyl)-2-trifluoromethanesulfonyl}naphthyl and (R)-1,1'-bi-{4,6-bis(tert-butyldiphenylsilyl)-2-trifluoromethanesulfonyl}naphthyl, and the corresponding enantiomers, or (S)-forms.

The optically active binaphthyl compound of the present invention shown by the formula (6b) is preferably such that $R^1$, $R^3$, $R^5$, and $R^6$ are each a hydrogen atom, and $R^2$ and $R^4$ are identical to one another and are each represented by the formula (2c). Of such compounds, particularly preferred are those in which in the formula (2c), $R^{13}$ and $R^{14}$ are each a methyl group, Pf is an n-octyl group having all the hydrogen atoms substituted with fluorine atoms, and n is 2.

Examples of the optically active binaphthyl compound of the present invention shown by the formula (6b) include (R)-1,1'-bi-{4-(2-perfluorooctylethyl)dimethylsilyl-2-trifluoromethanesulfonyl}naphthyl, (R)-1,1'-bi-{6-(2-perfluorooctylethyl)dimethylsilyl-2-trifluoromethanesulfonyl}naphthyl, (R)-1,1'-bi-{4-(2-perfluorooctylethyl)dimethylsilyl-6-(2-perfluorooctyl)ethyl-2-trifluoromethanesulfonyl}naphthyl, (R)-1,1'-bi-{4,6-bis[(2-perfluorooctylethyl)dimethylsilyl]-2-trifluoromethanesulfonyl}naphthyl and (R)-1,1'-bi-{4,6-bis[-tris(2-perfluorooctylethyl)silyl]-2-trifluoromethanesulfonyl}naphthyl, and the corresponding (S)-forms as enantiomers.

The optically active binaphthyl dimethyl ester compound of the present invention represented by the formula (5a) or (5b) can be obtained, for example, by reacting the optically active binaphthyl compound of the formula (6a) or (6b) with carbon monoxide and methanol in a proper solvent such as dimethyl sulfoxide in the presence of a palladium catalyst and an organic base, such as diisopropylethylamine, for capturing an acid, in a carbon monoxide atmosphere, which may be pressurized. The reaction is carried out at a substrate concentration of typically 5 to 30 wt % under a pressure of typically 1 to 30 atm, and preferably 5 to 20 atm, and at a temperature of typically room temperature to 200° C., and preferably 80° C. to 130° C., and is typically carried out over a time period of 24 to 72 hours. The palladium catalyst may have no valency or it may be prepared in the reaction system from a divalent acetate or the like. The palladium catalyst is typically used in an amount of 5 to 20 mol % relative to the substrate. The base is used in an amount of typically 2 to 8 equivalents, and preferably 2.5 to 5 equivalents, relative to the substrate. Methanol is used in an amount of 2 to 200 equivalents, and preferably 10 to 50 equivalents, relative to the substrate. In this manner, the desired diester product can be obtained in high yield.

While the optically active binaphthol compound of the present invention shown by the formula (7a) may be any of the compounds defined above, it preferably is a compound in which $R^1$, $R^3$, $R^5$, and $R^6$ are each a hydrogen atom, and $R^2$ and $R^4$ are identical to one another and are each represented by the formula (2a). Of these, most preferred are those in which $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

Examples of the optically active binaphthol compound of the present invention shown by the formula (7a) include, but are not limited to, (R)-1,1'-bi-{4,6-bis(trimethylsilyl)-2-hydroxy}naphthyl, (R)-1,1'-bi-{4,6-bis(triethylsilyl)-2-hydroxy}naphthyl, (R)-1,1'-bi-{4,6-bis(tripropylsilyl)-2-hydroxy}naphthyl, (R)-1,1'-bi-{4,6-bis(triisopropylsilyl)-2-hydroxy}naphthyl, (R)-1,1'-bi-{4,6-bis(tributylsilyl)-2-hydroxy}naphthyl, (R)-1,1'-bi-{4,6-bis(triphenylsilyl)-2-hydroxy}naphthyl, (R)-1,1'-bi-{4,6-bis(dimethyloctylsilyl)-2-hydroxy}naphthyl, (R)-1,1'-bi-{4,6-bis(tert-butyldimethylsilyl)-2-hydroxy}naphthyl, (R)-1,1'-bi-{4,6-bis(dimethylphenylsilyl)-2-hydroxy}naphthyl and (R)-1,1'-bi-{4,6-bis(tert-butyldiphenylsilyl)-2-hydroxy}naphthyl, and the corresponding (S)-forms as enantiomers.

The optically active binaphthol compound of the present invention shown by the formula (7b) is preferably such that $R^1$, $R^3$, $R^5$, and $R^6$ are each a hydrogen atom, and $R^2$ and $R^4$ are identical to one another and are each represented by the formula (2c). Of such compounds, particularly preferred are those in which $R^{13}$ and $R^{14}$ are each a methyl group, Pf is an n-octyl group with all the hydrogen atoms substituted with fluorine atoms, and n is 2 in the formula (2c).

Specific examples of the optically active binaphthol compound of the present invention shown by the formula (7b) include (R)-1,1'-bi-{2-hydroxy-4-(2-perfluorooctylethyl)dimethylsilyl}naphthyl, (R)-1,1'-bi-{2-hydroxy-6-(2-perfluorooctylethyl)dimethylsilyl}naphthyl, (R)-1,1'-bi-{2-hydroxy-4-(2-perfluorooctylethyl)dimethylsilyl-6-(2-perfluorooctyl)ethyl}naphthyl, (R)-1,1'-bi-{2-hydroxy-4,6-bis[(2-perfluorooctylethyl)dimethylsilyl]naphthyl and (R)-1,1'-bi-{2-hydroxy-4,6-bis[-tris(2-perfluorooctylethyl)silyl]}naphthyl, and the corresponding (S)-forms as enantiomers.

The optically active binaphthyl compound of the present invention represented by the formula (6a) or (6b) can be obtained, for example, by reacting the optically active binaphthol compound of the formula (7a) or (7b) with a triflating agent, such as a trifluoromethanesulfonic acid anhydride or trifluoromethanesulfonyl chloride, in an inert solvent such as dichloromethane in the presence of an organic base such as triethylamine. The reaction is typically carried out at a substrate concentration of 5 to 30 wt % and at a temperature of −78° C. to room temperature, and is typically carried out over a time period of 30 minutes to 3 hours. In this manner, the desired ditriflate product can be obtained in high yield.

While the optically active binaphthyl bis-methoxymethyl ether compound of the present invention shown by the formula (8a) may be any of the compounds defined above, it preferably is a compound in which $R^1$, $R^3$, $R^5$, and $R^6$ are each a hydrogen atom, and $R^2$ and $R^4$ are identical to one another and are each represented by the formula (2a). Of these, most preferred are those in which $R^{13}$, $R^{14}$, and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

Examples of the optically active binaphthyl diether compound of the present invention shown by the formula (8a) include, but are not limited to, (R)-1,1'-bi-{4,6-bis(trimethylsilyl)-2-methoxymethoxy}naphthyl, (R)-1,1'-bi-{4,6-bis(triethylsilyl)-2-methoxymethoxy}naphthyl, (R)-1,1'-bi-{4,6-bis(tripropylsilyl)-2-methoxymethoxy}naphthyl, (R)-1,1'-bi-{4,6-bis(triisopropylsilyl)-2-methoxymethoxy}naphthyl, (R)-1,1'-bi-{4,6-bis(tributylsilyl)-2-methoxymethoxy}naphthyl, (R)-1,1'-bi-{4,6-bis(triphenylsilyl)-2-methoxymethoxy}naphthyl, (R)-1,1'-bi-{4,6-bis(dimethyloctylsilyl)-2-methoxymethoxy}naphthyl, (R)-1,1'-bi-{4,6-bis(tert-butyldimethylsilyl)-2-methoxymethoxy}naphthyl, (R)-1,1'-bi-{4,6-bis(dimethylphenylsilyl)-2-methoxymethoxy}naphthyl and (R)-1,1'-bi-{4,6-bis(tert-butyldiphenylsilyl)-2-methoxymethoxy}naphthyl, and the corresponding (S)-forms as enantiomers.

The optically active binaphthyl bis-methoxymethyl ether compound of the present invention shown by the formula (8b) is preferably such that $R^1$, $R^3$, $R^5$, and $R^6$ are each a hydrogen atom, and $R^2$ and $R^4$ are identical to one another and are each represented by the formula (2c). Of such compounds, particularly preferred are those in which in the formula (2c), $R^{13}$ and $R^{14}$ are each a methyl group, Pf is an n-octyl group having all the hydrogen atoms substituted with fluorine atoms, and n is 2.

Examples of the optically active binaphthyl bis-methoxymethyl ether compound of the present invention shown by the formula (8b) include, but are not limited to, (R)-1,1'-bi-{2-methoxymethoxy-4-(2-perfluorooctylethyl)dimethylsilyl}naphthyl, (R)-1,1'-bi-{2-methoxymethoxy-6-(2-perfluorooctylethyl)dimethylsilyl}naphthyl, (R)-1,1'-bi-{2-methoxymethoxy-4-(2-perfluorooctylethyl)dimethylsilyl-6-(2-perfluorooctyl)ethyl}naphthyl, (R)-1,1'-bi-{2-methoxymethoxy-4,6-bis[(2-perfluorooctylethyl)dimethylsilyl]}naphthyl and (R)-1,1'-bi-{2-methoxymethoxy-4,6-bis[-tris(2-perfluorooctylethyl)silyl]}naphthyl, and the corresponding (S)-forms as enantiomers.

The optically active binaphthol compound of the present invention represented by the formula (7a) or (7b) can be obtained, for example, by reacting the optically active binaphthyl bis-methoxymethyl ether compound of the formula (8a) or (8b) with an organic acid, such as p-toluenesulfonic acid, in a proper solvent, such as dichloromethane and methanol, or a mixed solvent. Preferably, the organic acid is used in an amount of 2 to 3 equivalents relative to the substrate. The reaction is carried out at a substrate concentration of typically 5 to 20 wt % and at a temperature of typically 10° C. to 80° C., preferably 30° C. to 60° C., and is carried out over a time period of typically 20 minutes to 48 hours, and preferably 2 hours to 24 hours. In this manner, the desired binaphthol product can be obtained in high yield.

The optically active binaphthyl bis-methoxymethyl ether compound of the present invention represented by the formula (8a) can be obtained, for example, as follows: The optically active binaphthyl dieter compound of the formula (9a) is reacted with butyl lithium in a proper solvent, such as tetrahydrofuran, to replace the bromine atoms with lithium atoms. The reaction product is then reacted with the silyl chloride of the formula (10a) above, a compound represented by the following formula (10b):

$$Pf(CH_2)_n\text{—}Cl \qquad (10b)$$

(wherein Pf and n are as defined in the formula (2b) above, or the silyl chloride of the formula (10c) above. Using the alkyl lithium in an amount of typically 8 to 12 equivalents relative to the substrate, the reaction is carried out at a substrate concentration of typically 5 to 20 wt % and at a temperature of typically −100° C. to −50° C., and preferably −85° C. to −75° C., and is carried out over a time period of typically 20 minutes to 3 hours, and preferably 30 minutes to 2 hours. In this manner, the desired lithio product can be obtained. To this product, the alkyl silyl chloride is added, at the same temperature, in an amount of 4 to 8 equivalents relative to the substrate, and the reaction is carried out at a temperature of typically −80° C. to 30° C., and preferably 0° C. to room temperature, over a time period of typically 20 minutes to 2 hours, and preferably 30 minutes to 1 hour. In this manner, the desired product can be obtained in high yield.

While the optically active binaphthyl bis-methoxymethyl ether compound of the present invention shown by the formula (9a) or (9b) may be any of the compounds defined above, it preferably is a compound in which $R^1$, $R^3$, $R^5$ and $R^6$ are each a hydrogen atom.

While the silyl chloride of the present invention shown by the formula (10a) may be any of the compounds defined above, compounds are particularly preferred in which $R^{13}$, $R^{14}$, and $R^{15}$ are each independently a substituent selected from the group consisting of a methyl group, an ethyl group, an n-propyl group, an isopropyl group, an n-butyl group, an isobutyl group, a sec-butyl group, a tert-butyl group, an n-octyl group, and a phenyl group.

While the silyl chloride of the present invention shown by the formula (10c) may be any of the compounds defined above, compounds are particularly preferred in which $R^{13}$ and $R^{14}$ are each a methyl group, Pf is an n-octyl group with all the hydrogen atoms substituted with fluorine atoms, and n is 2 in the formula (2c).

The compound of the present invention represented by the formula (9a) can be obtained, for example, by reacting the compound of the formula (11a) with sodium hydride in a solvent, such as tetrahydrofuran, to form an alkoxide, followed by addition of chloromethylmethyl ether. The reaction is carried out at a substrate concentration of typically 5 to 20 wt % and at a temperature of typically −40° C. to room temperature, and preferably −10° C. to 0° C., and is carried out over a time period of typically 20 minutes to 3 hours, and preferably 30 minutes to 2 hours. In this manner, the desired product can be obtained in high yield. Of the compounds shown by the formula (9a), those in which $R^1$, $R^3$, $R^5$, and $R^6$ are each a hydrogen atom can be synthesized according to the process described in *J. Org. Chem.*, 2001, 66, 2358.

The compound of the present invention represented by the formula (9b) can be obtained by reacting a corresponding binaphthol product with sodium hydride in a solvent, such as tetrahydrofuran, to form an alkoxide, followed by addition of chloromethylmethyl ether. The reaction is carried out at a substrate concentration of typically 5 to 20 wt % and at a temperature of typically −40° C. to room temperature, and preferably −10° C. to 0° C., and is carried out over a time period of typically 20 minutes to 3 hours, and preferably 30 minutes to 2 hours. In this manner, the desired product can be obtained in high yield.

According to the present invention, the optically active quaternary ammonium salt of the formula (1a) or (1b) is used as a chiral phase-transfer catalyst.

In the stereoselective production of the compound of the formula (14), a Schiff base of a glycine ester shown by the formula (12) is asymmetrically alkylated with a halogenated alkyl of the formula (13) in a two-phase solvent system using the optically active quaternary ammonium salt of the formula (1a) or (1b) as a phase-transfer catalyst. The solvent used is a mixture of a water-immiscible hydrocarbon solvent, such as toluene, and a 40 to 60 wt % aqueous solution of an alkaline metal, such as potassium hydroxide and cesium hydroxide, with the ratio of the organic phase to the aqueous phase being in the range of 5:1 to 1:3, preferably, 5:1 to 1:1. This reaction is carried out at a substrate concentration of typically 5 to 20 wt % and at a temperature of typically −40° C. to 10° C., and preferably −25° C. to 5° C., and is carried out over a time period of typically 1 hour to 200 hours, and preferably 5 hours to 180 hours. The amount of the phase-transfer catalyst used is in the range of 0.2 to 2 mol %, and preferably in the range of 0.8 to 1.2 mol % relative to the substrate. In this manner, the desired optically active α-amino acid derivative can be obtained in high yield in a highly stereoselective manner.

In the above-describe process, the reaction product shown by the formula (16) is given as an (S)-form when the axially chiral, optically active quaternary ammonium salt of the formula (1a) or (1b) to serve as the phase-transfer catalyst has an absolute configuration of (R, R). Conversely, the product is given as an (R)-form when the catalyst has an absolute configuration of (S, S).

According to the present invention, the above-described process may be carried out in a three-phase solvent system comprising an organic solvent with the hydrogen atoms substituted with fluorine atoms, an organic solvent and water. The organic solvent with the hydrogen atoms substituted with fluorine atoms may be a fluorous solvent. Examples of fluorous solvent are perfluorinated alkanes and cycloalkanes, such as perfluorohexane and perfluoromethylcyclohexane. The fluorous solvent is added in an amount of 0.1 to 1.0 times by volume of the organic solvent used.

According to the present invention, the optically active quaternary ammonium salt of the formula (1b) can be recovered after it has been used in the reaction as a catalyst.

The ammonium salt can be recovered by using any proper technique: For example, it can be readily recovered by using an organic solvent, water, a mixed solvent of an organic solvent and water and/or an organic solvent with the hydrogen atoms substituted with fluorine atoms, to separate the optically active quaternary ammonium salt of the formula (1b) from a product (e.g., the reaction mixture of the above-described reaction) containing the ammonium salt. When necessary, the reaction mixture is diluted with water and an organic solvent, such as toluene, and is then subjected to separation with a fluorous solvent, such as perfluorinated alkanes and cycloalkanes, including perfluorohexane and perfluoromethylcyclohexane. In this manner, only the catalyst can be recovered from the fluorous layer in high yield.

According to the present invention, the recovered catalyst can be purified by removing the fluorous solvent from the fluorous solution by distillation, and subjecting the residue to a silica gel column chromatography using a relatively high polar organic solvent, such as a mixed solvent of dichloromethane/methanol, as an eluant. The crude recovered product obtained by concentrating the fluorous solvent may be directly used as a catalyst in the subsequent reaction.

EXAMPLES

The present invention will now be described in further detail with reference to examples of axially chiral, optically active spiro-quaternary ammonium salts represented by the formula (1a). These examples, however, are provided by way of example only and are not intended to limit the scope of the invention in any way.

Example 1

Synthesis of (R)-1,1'-bi-(4,6-dibromo-2-methoxymethoxy)naphthyl (2)

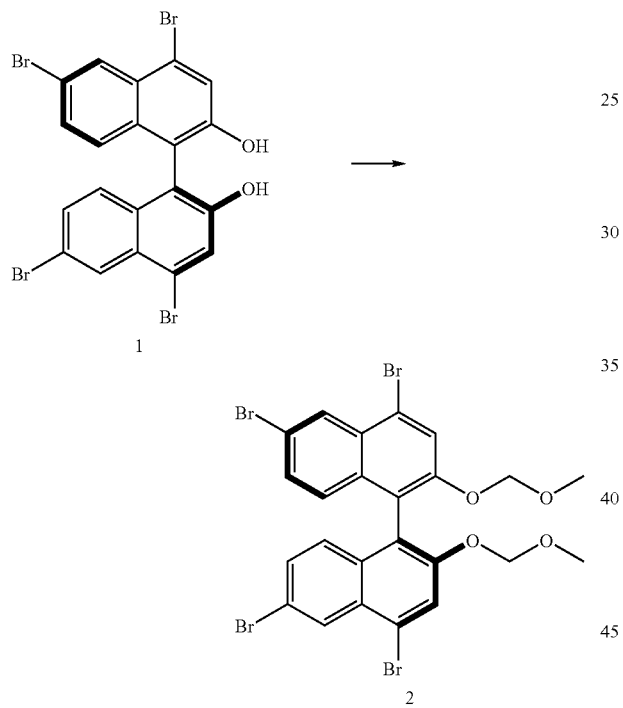

In an argon atmosphere, 60% sodium hydride (0.880 g, 22 mmol) was added to a tetrahydrofuran solution (50 mL) of Compound 1 (6.02 g, 10 mmol) at 0° C. and the mixture was stirred for 10 minutes. Subsequently, chloromethyl ether (1.67 mL, 22 mmol) was added at 0° C., and the reaction mixture was allowed to warm to room temperature and was then stirred for 1 hour. After completion of the reaction, the reaction mixture was poured into water and was extracted with dichloromethane. The dichloromethane solution was dried over anhydrous sodium sulfate and was concentrated under reduced pressure. To the resulting white solid, hexane (30 mL) was added and the solution was filtered to give Compound 2 (6.90 g, 10 mmol) in a quantitative manner.

$^1$H-NMR (400 MHz, CDCl$_3$) σ 8.43 (2H, d, J=2.4 Hz, Ar—H), 7.94 (2H, s, Ar—H), 7.33 (2H, dd, J=2.4 Hz, 9.2 Hz, Ar—H), 6.96 (2H, d, J=9.2 Hz, Ar—H), 5.07 (2H, d, J=7.2 Hz, Ar—OCH$_2$), 4.98 (2H, d, J=7.2 Hz, Ar—OCH$_2$), 3.20 (6H, s, OCH$_3$)

Examples 2 through 6

Synthesis of (R)-1,1'-bi-{4,6-bis(trialkylsilyl)-2-methoxymethoxy}naphthyls (3a through 3e)

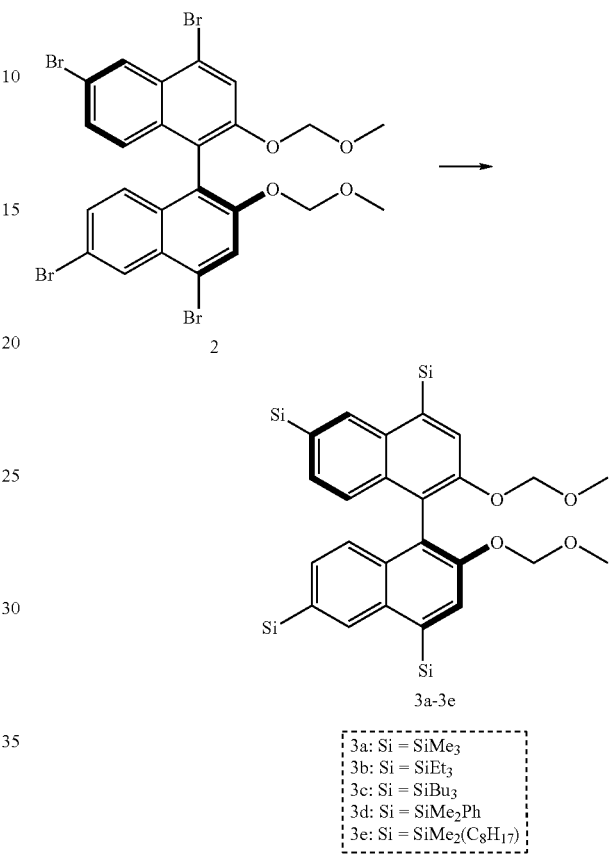

3a: Si = SiMe$_3$
3b: Si = SiEt$_3$
3c: Si = SiBu$_3$
3d: Si = SiMe$_2$Ph
3e: Si = SiMe$_2$(C$_8$H$_{17}$)

In an argon atmosphere, a 1.40M tert-butyllithium solution (1.93 mL, 2.7 mmol) was added dropwise to a tetrahydrofuran solution (10 mL) of Compound 2 (0.207 g, 0.30 mmol) at −78° C., and the mixture was stirred for 15 minutes. Subsequently, a corresponding trialkylchlorosilane (1.80 mmol) was added at −78° C., and the reaction mixture was allowed to warm to room temperature and was then stirred for 4 hours. After completion of the reaction, the reaction mixture was poured into water and was extracted with dichloromethane. The dichloromethane solution was dried over anhydrous sodium sulfate and was concentrated under reduced pressure. The resulting residue was subjected to a silica gel column chromatography and eluted with a mixed solvent of diethylether/hexane to give Compounds 3a through 3e in yields of 60 to 85%.

Chemical data for the products of Examples 2 through 6 are shown below.

Product of Example 2 (Compound 3a)

(R)-1,1'-bi-{4,6-bis(trimethylsilyl)-2-methoxymethoxy}naphthyl: $^1$H-NMR (400 MHz, CDCl$_3$) σ 8.29 (2H, s, Ar—H), 7.72 (2H, s, Ar—H), 7.31 (2H, dd, J=1.2 Hz, 8.4 Hz, Ar—H), 7.16(2H, d, J=8.4 Hz, Ar—H), 5.03 (2H, d, J=6.4 Hz, Ar—OCH$_2$), 4.95 (2H, d, J=6.4 Hz, Ar—OCH$_2$), 3.15 (6H, s, OCH$_3$), 0.55 (18H, s, SiCH$_3$), 0.27 (18H, s, SiCH$_3$).

Product of Example 3 (Compound 3b)

(R)-1,1'-bi-{4,6-bis(triethylsilyl)-2-methoxymethoxy}naphthyl: $^1$H-NMR (400 MHz, CDCl$_3$) σ 8.24 (2H, s, Ar—H), 7.67 (2H, s, Ar—H), 7.31 (2H, dd, J=1.2 Hz, 8.4 Hz, Ar—H), 7.19 (2H, d, J=8.4 Hz, Ar—H), 5.04 (2H, d, J=6.4 Hz, Ar—OCH$_2$), 4.91 (2H, d, J=6.4 Hz, Ar—OCH$_2$), 2.97 (6H, s, OCH$_3$), 1.40-0.80 (60H, m, SiCH$_2$CH$_3$).

Product of Example 4 (Compound 3c)

(R)-1,1'-bi-{4,6-bis(tributylsilyl)-2-methoxymethoxy}naphthyl: $^1$H-NMR (400 MHz, CDCl$_3$) σ 8.25 (2H, s, Ar—H), 7.64 (2H, s, Ar—H), 7.31 (2H, d, J=8.4 Hz, Ar—H), 7.21 (2H, d, J=8.4 Hz, Ar—H), 5.04 (2H, d, J=6.4 Hz, Ar—OCH$_2$), 4.89 (2H, d, J=6.4 Hz, Ar—OCH$_2$), 2.89 (6H, s, OCH$_3$), 1.39-0.80 (108H, m, SiCH$_2$CH$_2$CH$_2$CH$_3$).

Product of Example 5 (Compound 3d)

(R)-1,1'-bi-{4,6-bis(dimethylphenylsilyl)-2-methoxymethoxy}naphthyl: $^1$H-NMR (400 MHz, CDCl$_3$) σ 8.05 (2H, s, Ar—H), 7.33 (2H, s, Ar—H), 7.59-7.28 (22H, m, Ar—H), 7.10 (2H, d, J=8.4 Hz, Ar—H), 5.97 (2H, d, J=6.4 Hz, Ar—OCH$_2$), 4.88 (2H, d, J=6.4 Hz, Ar—OCH$_2$), 3.04 (6H, s, OCH$_3$), 0.67 (12H, s, SiCH$_3$), 0.41 (12H, s, SiCH$_3$).

Product of Example 6 (Compound 3e)

(R)-1,1'-bi-{4,6-bis(dimethyloctylsilyl)-2-methoxymethoxy}naphthyl: $^1$H-NMR (400 MHz, CDCl$_3$) σ 8.27 (2H, s, Ar—H), 7.70 (2H, s, Ar—H), 7.30 (2H, dd, J=1.2 Hz, 8.4 Hz, Ar—H), 7.16 (2H, d, J=8.4 Hz, Ar—H), 5.03 (2H, d, J=6.4 Hz, Ar—OCH$_2$), 4.93 (2H, d, J=6.4 Hz, Ar—OCH$_2$), 3.09 (6H, s, OCH$_3$), 1.45-0.72 (68H, m, SiC$_8$H$_{17}$), 0.48 (12H, s, SiCH$_3$), 0.27 (12H, s, SiCH$_3$).

Example 7

Synthesis of (R)-1,1'-bi-{4,6-bis(triethylsilyl)-2-hydroxy}naphthyl (4b)

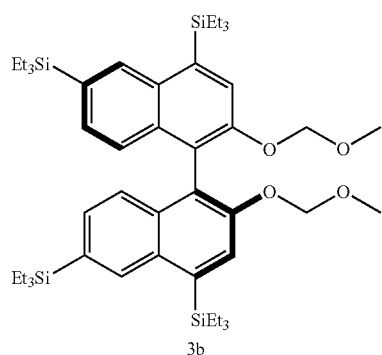

3b

-continued

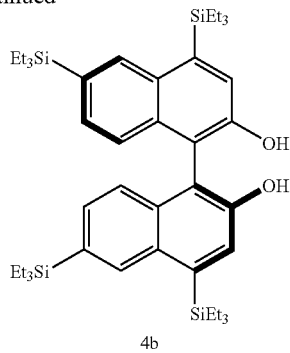

4b p-toluenesulfonic acid monohydrate (0.114 g, 0.60 mmol) was added to Compound 3b (0.30 mmol) in dichloromethane (10 mL) and methanol (10 mL) at room temperature, and the mixture was stirred at 50° C. for 24 hours. After completion of the reaction, the reaction mixture was poured into water and was extracted with dichloromethane. The dichloromethane solution was dried over anhydrous sodium sulfate and was concentrated under reduced pressure to give Compound 4b in a quantitative yield.

$^1$H-NMR (400 MHz, CDCl$_3$) σ 8.28 (2H, s, Ar—H), 7.54 (2H, s, Ar—H), 7.39 (2H, dd, J=1.2 Hz, 8.4 Hz, Ar—H), 7.29 (2H, d, J=8.4 Hz, Ar—H), 4.99 (2H, s, OH), 1.11-0.80 (60H, m, SiCH$_2$CH$_3$)

Examples 8 through 11

Synthesis of (R)-1,1'-bi-{4,6-bis(trialkylsilyl)-2-hydroxy}naphthyls (4a, 4c, 4d, and 4e)

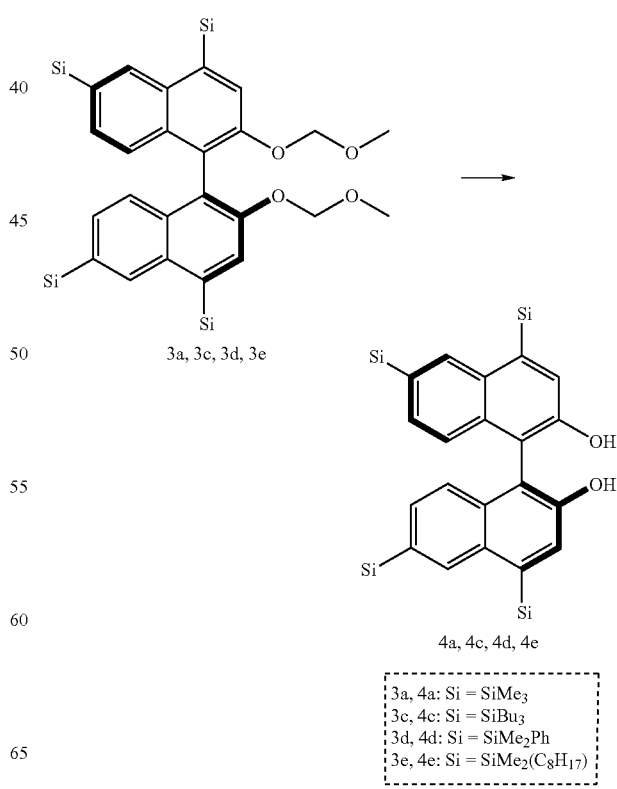

3a, 3c, 3d, 3e 4a, 4c, 4d, 4e 3a, 4a: Si = SiMe$_3$
3c, 4c: Si = SiBu$_3$
3d, 4d: Si = SiMe$_2$Ph
3e, 4e: Si = SiMe$_2$(C$_8$H$_{17}$)

To obtain Compounds 4a, 4c, 4d, and 4e in quantitative yields, the same procedure was followed as in Example 7, except that Compound 3a, 3c, 3d, or 3e was used as the starting material in place of Compound 3b.

Example 12

Synthesis of (R)-1,1'-bi-{4,6-bis(triethylsilyl)-2-trifluoromethanesulfonyl}naphthyl (5b)

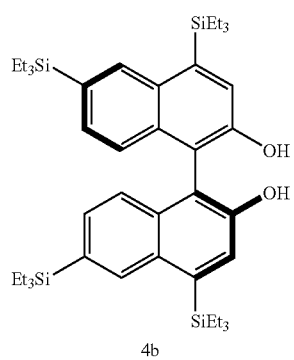

4b

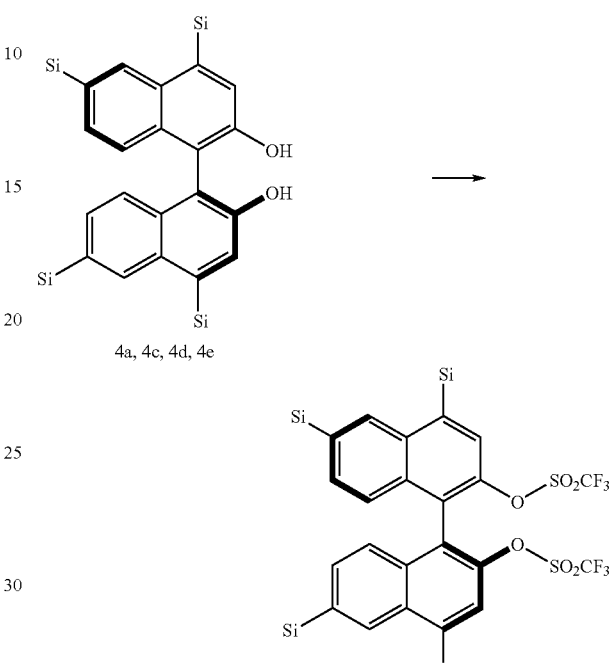

5b

In an argon atmosphere, triethylamine (11.1 mmol) was added to a dichloromethane solution (25 mL) of Compound 4b (3.70 mmol), and the mixture was cooled to −78° C. Trifluoromethanesulfonic-acid anhydride (11.1 mmol) was added dropwise, and the mixture was allowed to warm to room temperature, followed by stirring for 1 hour. Subsequently, the reaction mixture was poured into a saturated aqueous solution of ammonium chloride and the solution was extracted with dichloromethane. The dichloromethane solution was dried over anhydrous sodium sulfate and was concentrated under reduced pressure. After concentration, the resulting residue was subjected to a silica gel column chromatography and eluted with a mixed solvent of diethylether/hexane to give Compound 5b in a quantitative yield.

$^1$H-NMR (400 MHz, CDCl$_3$) σ 8.35 (2H, s, Ar—H), 7.71 (2H, s, Ar—H), 7.47 (2H, dd, J=1.2 Hz, 8.4 Hz, Ar—H), 7.30 (2H, d, J=8.4 Hz, Ar—H), 1.11-0.85 (60H, m, SiCH$_2$CH$_3$).

Examples 13 through 16

Synthesis of (R)-1,1'-bi-{4,6-bis(trialkylsilyl)-2-trifluoromethanesulfonyl}naphthyls (5a, 5c, 5d, and 5e)

4a, 5a: Si = SiMe$_3$
4c, 5c: Si = SiBu$_3$
4d, 5d: Si = SiMe$_2$Ph
4e, 5e: Si = SiMe$_2$(C$_8$H$_{17}$)

To obtain Compounds 5a, 5c, 5d, and 5e in quantitative yields, the same procedure was followed as in Example 12, except that Compound 4a, 4c, 4d, or 4e was used as the starting material in place of Compound 4b.

Examples 17 through 21

Synthesis of (R)-1,1'-bi-{4,6-bis(trialkylsilyl)-2-methoxycarbonyl}naphthyls (6a through 6e)

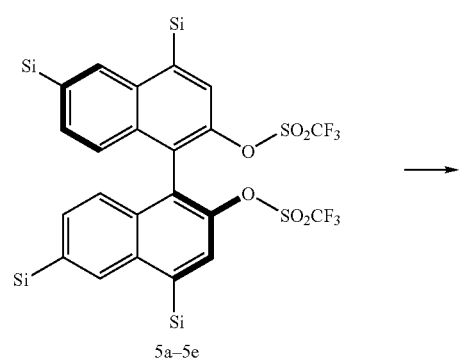

5a–5e

-continued

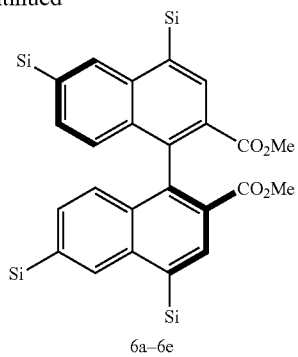

6a–6e 5a, 6a: Si = SiMe₃
    5b, 6b: Si = SiEt₃
    5c, 6c: Si = SiBu₃
    5d, 6d: Si = SiMe₂Ph
    5e, 6e: Si = SiMe₂(C₈H₁₇)

In an argon atmosphere, iPr₂NEt (0.51 mL), MeOH (1.0 mL) and DMSO (2.0.mL) were added to a mixture containing one of Compounds 5a through 5e (0.70 mmol), Pd(OAc)₂ (15 mol %), and dppp (16.5 mol %). While the reaction vessel was pressurized to 15 atm under CO atmosphere, the mixture was stirred at 100° C. for 24 hours. Subsequently, the reaction mixture was poured into water and the solution was extracted with ethyl acetate. The extract was dried over anhydrous sodium sulfate and was concentrated under reduced pressure. After concentration, the resulting residue was subjected to a silica gel column chromatography and eluted with a mixed solvent of diethylether/hexane to give Compounds 6a through 6e in yields of 58 to 80%.

Chemical data for the products of Examples 17 through 21 are shown below.

Product of Example 17 (Compound 6a)

(R)-1,1'-bi-{4,6-bis(trimethylsilyl)-2-methoxycarbonyl}naphthyl: $^1$H-NMR (400 MHz, CDCl₃) σ 8.34 (2H, s, Ar—H), 8.33 (2H, s, Ar—H), 7.31 (2H, d, J=8.4 Hz, Ar—H), 7.03 (2H, d, J=8.4 Hz, Ar—H), 3.53 (6H, s, CO₂CH₃), 0.57 (18H, s, SiCH₃), 0.30 (18H, s, SiCH₃).

Product of Example 18 (Compound 6b)

(R)-1,1'-bi-{4,6-bis(triethylsilyl)-2-methoxycarbonyl}naphthyl: $^1$H-NMR (400 MHz, CDCl₃) σ 8.31 (2H, s, Ar—H), 8.28 (2H, s, Ar—H), 7.32 (2H, dd, J=1.2 Hz, 8.4 Hz, Ar—H), 7.11 (2H, d, J=8.4 Hz, Ar—H), 3.32 (6H, S, CO₂CH₃), 1.12-0.82 (60H, m, SiCH₂CH₃).

Product of Example 19 (Compound 6c)

(R)-1,1'-bi-{4,6-bis(tributylsilyl)-2-methoxycarbonyl}naphthyl: $^1$H-NMR (400 MHz, CDCl₃) σ 8.32 (2H, s, Ar—H), 8.27 (2H, s, Ar—H), 7.32 (2H, d, J=8.4 Hz, Ar—H), 7.13 (2H, d, J=8.4 Hz, Ar—H), 3.27 (6H, S, CO₂CH₃), 1.38-0.81 (108H, m, SiCH₂CH₂CH₂CH₃).

Product of Example 20 (Compound 6d)

(R)-1,1'-bi-{4,6-bis(dimethylphenylsilyl)-2-methoxycarbonyl}naphthyl: $^1$H-NMR (400 MHz, CDCl₃) σ 8.40 (2H, s, Ar—H), 8.11 (2H, s, Ar—H), 7.52 (2H, d, J=8.4 Hz, Ar—H), 7.38-7.22 (20H, m, Ar—H), 7.10 (2H, d, J=8.4 Hz, Ar—H), 3.49 (6H, S, CO₂CH₃), 0.70 (12H, s, SiCH₃), 0.37 (12H, s, SiCH₃).

Product of Example 21 (Compound 6e)

(R)-1,1'-bi-{4,6-bis(dimethyloctylsilyl)-2-methoxycarbonyl}naphthyl: $^1$H-NMR (400 MHz, CDCl₃) σ 8.33 (2H, s, Ar—H), 8.30 (2H, s, Ar—H), 7.29 (2H, dd, J=1.2 Hz, 8.4 Hz, Ar—H), 7.04 (2H, d, J=8.4 Hz, Ar—H), 3.47 (6H, S, CO₂CH₃), 1.43-0.75 (68H, m, SiC₈H₁₇), 0.55 (12H, s, SiCH₃), 0.28 (12H, s, SiCH₃).

Example 22

Synthesis of (R)-1,1'-bi-{4,6-bis(triethylsilyl)-2-hydroxymethyl}naphthyl (7b)

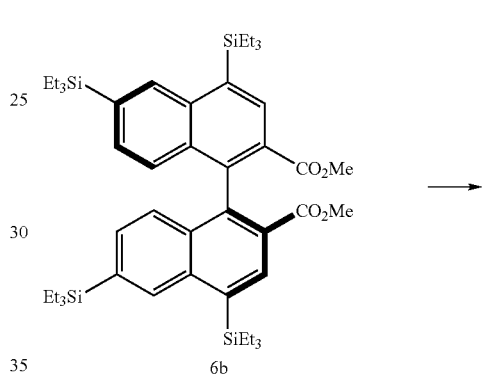

6b

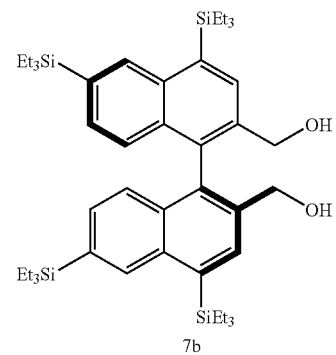

7b

In an argon atmosphere, Compound 6b (0.44 mmol) was added to a tetrahydrofuran solution of LiAlH₄ (1.30 mmol) at 0° C., and the mixture was stirred for 1 hour. Subsequently, the reaction mixture was deactivated by sequentially adding MeOH and a saturated aqueous solution of ammonium chloride and the solution was extracted with diethylether. The extract was dried over anhydrous sodium sulfate and was concentrated under reduced pressure. The resulting residue was subjected to a silica gel column chromatography and eluted with a mixed solvent of diethylether/hexane to give Compound 7b in a quantitative yield.

$^1$H-NMR (400 MHz, CDCl₃) σ 8.31 (2H, s, Ar—H), 7.84 (2H, s, Ar—H), 7.32 (2H, dd, J=1.2 Hz, 8.4 Hz, Ar—H), 7.05

(2H, d, J=8.4 Hz, Ar—H), 4.42 (2H, d, J=11.6 Hz, ArCH$_2$), 4.16 (2H, d, J=11.6 Hz, ArCH$_2$), 2.86 (2H, br s, OH), 1.13-0.80 (60H, m, SiCH$_2$CH$_3$).

Examples 23 through 26

Synthesis of (R)-1,1'-bi-{4,6-bis(trialkylsilyl)-2-hydroxymethyl}naphthyls (7a, 7c, 7d, and 7e)

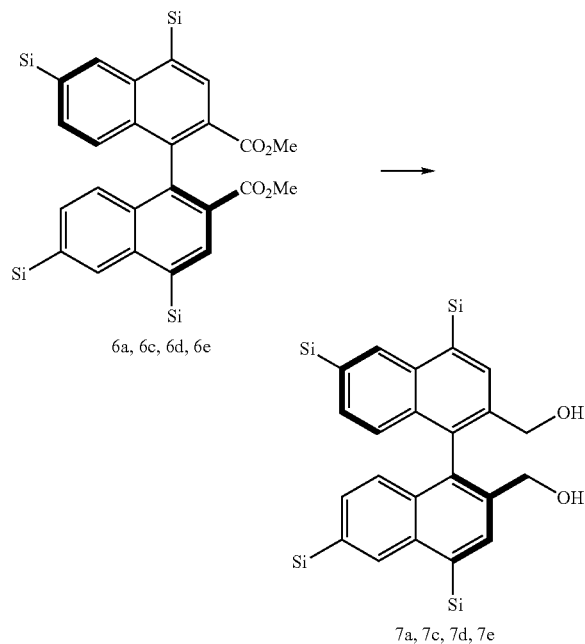

6a, 7a: Si = SiMe$_3$
6c, 7c: Si = SiBu$_3$
6d, 7d: Si = SiMe$_2$Ph
6e, 7e: Si = SiMe$_2$(C$_8$H$_{17}$)

To obtain Compounds 7a, 7c, 7d, and 7e in quantitative yields, the same procedure was followed as in Example 22, except that Compound 6a, 6c, 6d, or 6e was used as the starting material in place of Compound 6b.

Example 27

Synthesis of (R)-1,1'-bi-{4,6-bis(triethylsilyl)-2-bromomethyl}naphthyl (8b)

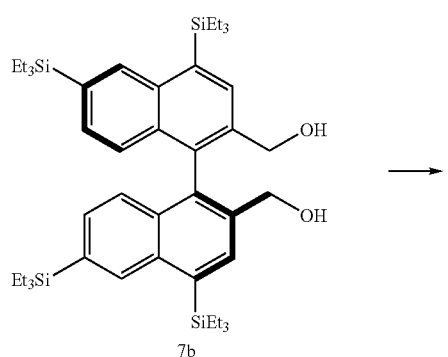

7b

-continued

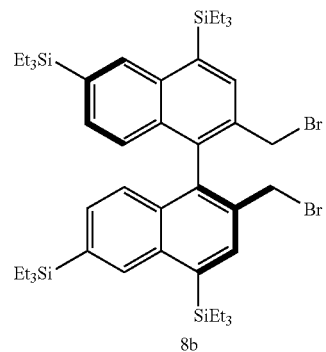

8b

Triphenylphosphine (0.315 g, 1.2 mmol) and carbon tetrabromide (0.398 g, 1.2 mmol) were added to a tetrahydrofuran solution (10 mL) of Compound 7b (0.20 mmol), and the mixture was stirred at room-temperature for 4 hours. After completion of the reaction, the reaction mixture was poured into water and was extracted with dichloromethane. The dichloromethane solution was dried over anhydrous sodium sulfate and was concentrated under reduced pressure. After concentration, the residue was subjected to a silica gel column chromatography and was eluted with a hexane solvent to give Compound 8b in a quantitative yield.

$^1$H-NMR (400 MHz, CDCl$_3$) σ 8.28 (2H, s, Ar—H), 7.87 (2H, s, Ar—H), 7.34 (2H, dd, J=1.2 Hz, 8.4 Hz, Ar—H), 7.06 (2H, d, J=8.4 Hz, Ar—H), 4.24 (4H, s, ArCH$_2$), 1.13-0.80 (60H, m, SiCH$_2$CH$_3$).

Examples 28 through 31

Synthesis of (R)-1,1'-bi-{4,6-bis(trialkylsilyl)-2-bromomethyl}naphthyls (8a, 8c, 8d, and 8e)

7a, 7c, 7d, 7e

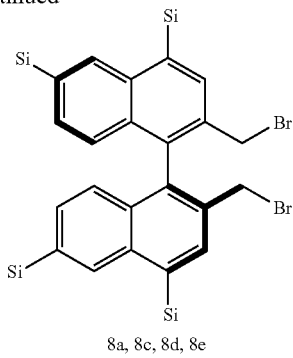

8a, 8c, 8d, 8e

```
7a, 8a: Si = SiMe₃
7c, 8c: Si = SiBu₃
7d, 8d: Si = SiMe₂Ph
7e, 8e: Si = SiMe₂(C₈H₁₇)
```

To obtain Compounds 8a, 8c, 8d, and 8e in quantitative yields, the same procedure was followed as in Example 27, except that Compound 7a, 7c, 7d, or 7e was used as the starting material in place of Compound 7b.

Examples 32 through 36

Synthesis of spiro-bis[{(R)-1,1'-bi-{4,6-bis(trimethylsilyl)naphthyl}}2,2'-dimethyl]ammonium bromides (9a through 9e)

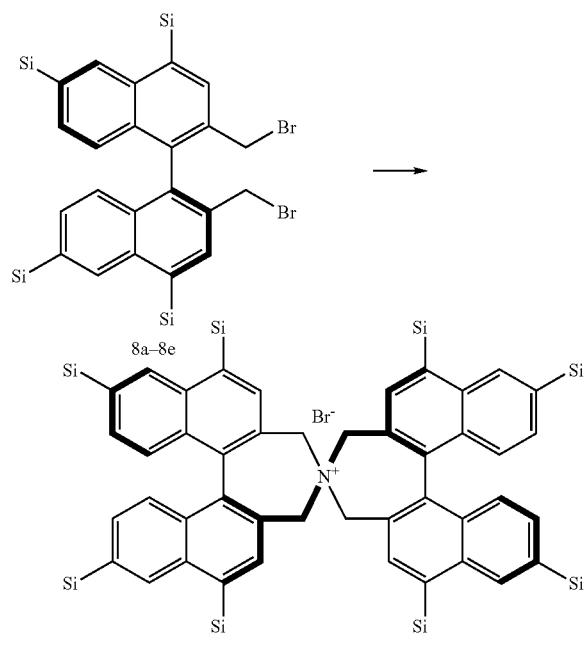

9a–9e

```
8a, 9a: Si = SiMe₃
8b, 9b: Si = SiEt₃
8c, 9c: Si = SiBu₃
8d, 9d: Si = SiMe₂Ph
8e, 9e: Si = SiMe₂(C₈H₁₇)
```

A 28% aqueous ammonia (0.77 mL, 12.6 mmol) and acetonitrile (5 mL) were added to one of Compounds 8a through 8e (3.15 mmol). The reaction vessel was sealed and the mixture was stirred for 24 hours while being refluxed. Subsequently, the reaction mixture was poured into water and the solution was extracted with dichloromethane. The extract was dried over anhydrous sodium sulfate and was concentrated under reduced pressure. After concentration, the resulting residue was subjected to a silica gel column chromatography and eluted with a mixed solvent of dichloromethane/methanol to give Compounds 9a through 9e in yields of 25 to 65%.

Chemical data for the products of Examples 32 through 36 are shown below.

Product of Example 32 (Compound 9a)

Spiro-bis[{(R)-1,1'-bi-{4,6-bis(trimethylsilyl)naphthyl}}-2,2'-dimethyl]ammonium bromide: $^1$H-NMR (400 MHz, CDCl$_3$) σ 8.50 (4H, s, Ar—H), 7.80 (4H, s, Ar—H), 7.44 (4H, d, J=8.8 Hz, Ar—H), 7.30 (4H, d, J=8.8 Hz, Ar—H), 4.46 (4H, d, J=14.0 Hz, ArCH$_2$), 4.10 (4H, d, J=14.0 Hz, ArCH$_2$), 0.73 (36H, s, SiCH$_3$), 0.36 (36H, s, SiCH$_3$).

Product of Example 33 (Compound 9b)

Spiro-bis[{(R)-1,1'-bi-{4,6-bis(triethylsilyl)naphthyl}}-2,2'-dimethyl]ammonium bromide: $^1$H-NMR (400 MHz, CDCl$_3$) σ 8.48 (4H, s, Ar—H), 7.91 (4H, s, Ar—H), 7.43 (4H, dd, J=1.2 Hz, 8.4 Hz, Ar—H), 7.25 (4H, d, J=8.4 Hz, Ar—H), 4.38 (4H, d, J=13.2 Hz, ArCH$_2$), 4.08 (4H, d, J=13.2 Hz, ArCH$_2$), 1.32-0.85 (120H, m, SiCH$_2$CH$_3$).

Product of Example 34 (Compound 9c)

Spiro-bis[{(R)-1,1'-bi-{4,6-bis(tributylsilyl)naphthyl}}-2,2'-dimethyl]ammonium bromide: $^1$H-NMR (400 MHz, CDCl$_3$) σ 8.47 (4H, s, Ar—H), 7.85 (4H, s, Ar—H), 7.36 (4H, d, J=8.4 Hz, Ar—H), 7.13 (4H, d, J=8.4 Hz, Ar—H), 4.39 (4H, d, J=13.6 Hz, ArCH$_2$), 4.15 (4H, d, J=13.6 Hz, ArCH$_2$), 1.43-0.85 (108H, m, SiCH$_2$CH$_2$CH$_2$CH$_3$).

Product of Example 35 (Compound 9d)

Spiro-bis[{(R)-1,1'-bi-{4,6-bis(dimethylphenylsilyl)naphthyl}}-2,2'-dimethyl]ammonium bromide: $^1$H-NMR (400 MHz, CDCl$_3$) σ 8.23 (4H, s, Ar—H), 8.18 (4H, s, Ar—H), 7.57-7.21 (48H, m, Ar—H), 4.61 (4H, d, J=13.6 Hz, ArCH$_2$), 4.27 (4H, d, J=13.6 Hz, ArCH$_2$), 0.81 (12H, s, SiCH$_3$), 0.74 (12H, s, SiCH$_3$), 0.39 (12H, s, SiCH$_3$), 0.38 (12H, s, SiCH$_3$).

Product of Example 36 (Compound 9e)

Spiro-bis[{(R)-1,1'-bi-{4,6-bis(dimethyloctylsilyl)naphthyl}}-2,2'-dimethyl]ammonium bromide: $^1$H-NMR (400 MHz, CDCl$_3$) σ 8.47 (4H, s, Ar—H), 7.96 (4H, s, Ar—H), 7.41 (4H, d, J=8.4 Hz, Ar—H), 7.26 (4H, d, J=8.4 Hz, Ar—H), 4.43 (4H, d, J=13.2 Hz, ArCH$_2$), 4.11 (4H, d, J=13.2 Hz, ArCH$_2$), 1.53-0.80 (136H, m, SiC$_8$H$_{17}$), 0.73 (12H, s, SiCH$_3$), 0.70 (12H, s, SiCH$_3$), 0.35 (12H, s, SiCH$_3$), 0.34 (12H, s, SiCH$_3$).

Examples 37 through 52

Asymmetric Alkylation Using Compounds (9a) Through (9e) as an Optically Active Phase-transfer Catalyst

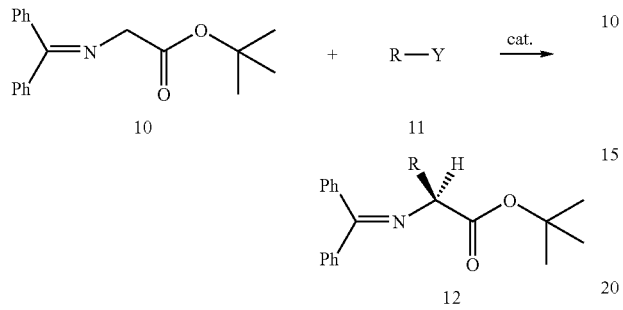

At 0° C., Compound 11 (0.6 mmol) of the formula (13) shown as R—Y in Table 1 was added to a mixture of Compound 10 of the formula (12) (0.5 mmol), a phase-transfer catalyst (one of Compound (9a), Compound (9b), Compound (9c), Compound (9d), and Compound (9e)) (0.05 mmol), toluene (3.3 mL), and a 50% aqueous solution of potassium hydroxide (1.0 mL). The mixture was stirred at the same temperature and was poured into water. The solution was extracted with ether and the extract was washed with saturated brine, followed by drying over sodium sulfate and concentration under reduced pressure. The resulting residue was subjected to a silica gel column chromatography to give an alkylated compound 12 of the formula (14). The results obtained for different phase-transfer catalysts and different alkylating agents were collectively shown in Table 1.

The optical purity of the reaction products was determined according to the technique described in *J. Am. Chem. Soc.* 1999, Vol. 121, No. 27, 6519-6520.

TABLE 1

| Examples | R-Y | Cat. | Time [h] | Yield [%] | Ee [%] |
|---|---|---|---|---|---|
| 37 | PhCH$_2$Br | 9e | 172 | 96 | 99 |
| 38 | " | 9d | 26 | 98 | 98 |
| 39 | " | 9c | 50 | 92 | 99 |
| 40 | " | 9b | 6 | 97 | 97 |
| 41 | " | 9a | 96 | 60 | 92 |
| 42 | MeI | 9e | 14 | 92 | 93 |
| 43 | " | 9d | 16 | 92 | 92 |
| 44 | " | 9c | 10 | 93 | 88 |
| 45 | " | 9b | 22 | 90 | 89 |
| 46 | " | 9a | 10 | 92 | 92 |
| 47 | CH$_2$=CHCH$_2$Br | 9e | 96 | 98 | 98 |
| 48 | HC≡CCH$_2$Br | 9e | 32 | 96 | 99 |
| 49 | EtI | 9e | 10 | 87 | 98 |
| 50 | HexI | 9e | 10 | 81 | 97 |
| 51 | iPr-I | 9e | 15 | 70 | 95 |
| 52 | cPent-I | 9e | 15 | 75 | 96 |

The present invention will now be described in further detail with reference to examples of fluorine-containing, optically active quaternary ammonium salts represented by the formula (1b). These examples, however, are provided by way of example only and are not intended to limit the scope of the invention in any way.

Example 53

Synthesis of (R)-1,1'-bi-{4,6-bis(2-perfluorooctyl-ethyldimethylsilyl)-2-methoxymethoxy}naphthyl (3)

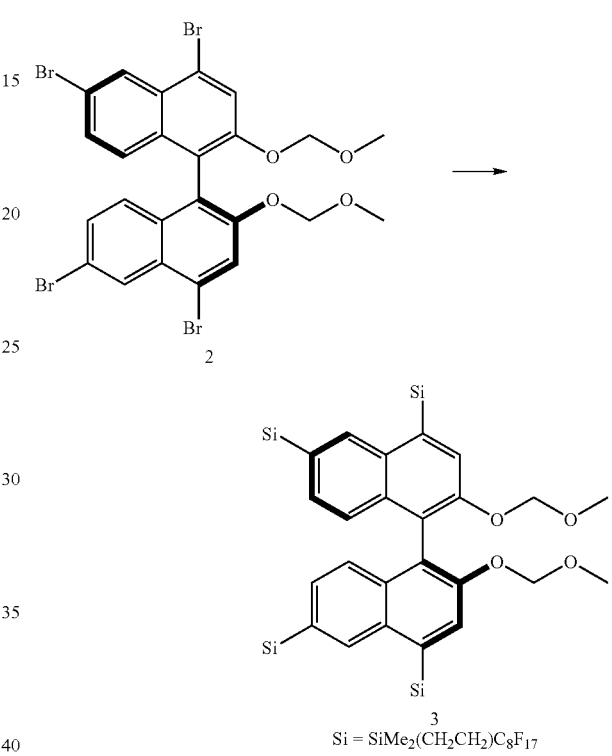

In an argon atmosphere, a 1.40M tert-butyllithium solution (1.93 mL, 2.7 mmol) was added dropwise to a tetrahydrofuran solution (10 mL) of Compound 2 (0.207 g, 0.30 mol) at −78° C. and the mixture was stirred for 15 minutes. Subsequently, dimethyl(perfluorooctyl)ethylchlorosilane (1.80 mmol) was added at −78° C., and the reaction mixture was allowed to warm to room temperature and was then stirred for 4 hours. After completion of the reaction, the reaction mixture was poured into water and was extracted with dichloromethane. The dichloromethane solution was dried over anhydrous sodium sulfate and was concentrated under reduced pressure. After concentration, the residue was subjected to a silica gel column chromatography and eluted with a mixed solvent of diethylether/hexane to give Compound 3 in a yield of 85%. Chemical data for the product are shown below.

$^1$H-NMR (400 MHz, CDCl$_3$) σ 8.21 (2H, s, Ar—H), 7.74 (2H, s, Ar—H), 7.30 (2H, d, J=8.4 Hz, Ar—H), 7.18 (2H, d, J=8.4 Hz, Ar—H) ,5.07 (2H, d, J=6.8 Hz, Ar—OCH$_2$), 4.95 (2H, d, J=6.8 Hz, Ar—OCH$_2$), 3.10 (6H, s, OCH$_3$), 2.16-1.95 (8H, m, CH$_2$CF$_2$), 1.32-1.27 (4H, m, SiCH$_2$), 1.02-0.98 (4H, m, SiCH$_2$), 0.61 (12H, s, SiCH$_3$), 0.37 (6H, s, SiCH$_3$), 0.36 (6H, s, SiCH$_3$).

Example 54

Synthesis of (R)-1,1'-bi-{4,6-bis(2-perfluorooctyl-ethyldimethylsilyl)-2-hydroxy}naphthyl (4)

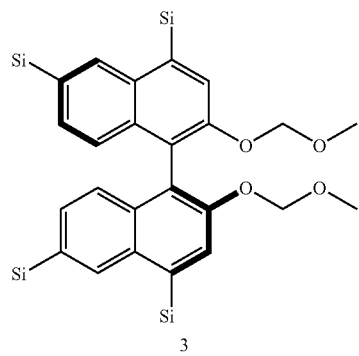

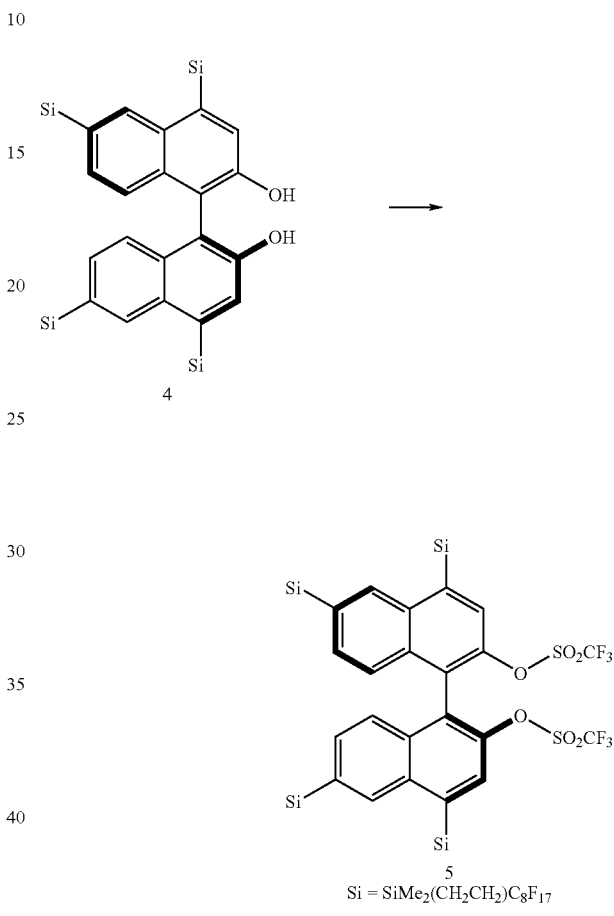

p-toluenesulfonic acid monohydrate (0.114 g, 0.60 mmol) was added to Compound 3 (0.30 mmol) in dichloromethane (10 mL) and methanol (10 mL) at room temperature, and the mixture was stirred at 50° C. for 24 hours. After completion of the reaction, the reaction mixture was poured into water and was extracted with dichloromethane. The dichloromethane solution was dried over anhydrous sodium sulfate and was concentrated under reduced pressure to give Compound 4 in a quantitative yield. The chemical data for the product are shown below.

$^1$H-NMR (400 MHz, CDCl$_3$) σ 8.23 (2H, s, Ar—H), 7.58 (2H, s, Ar—H), 7.39 (2H, d, J=8.4 Hz, Ar—H), 7.20 (2H, d, J=8.4 Hz, Ar—H), 5.01 (2H, s, OH), 2.13-1.97 (8H, m, CH$_2$CF$_2$), 1.33-1.28 (4H, m, SiCH$_2$), 1.04-0.99 (4H, m, SiCH$_2$), 0.61 (12H, s, SiCH$_3$), 0.37 (12H, s, SiCH$_3$).

Example 55

Synthesis of (R)-1,1'-bi-{4,6-bis(2-perfluorooctyl-ethyldimethylsilyl)-2-trifluoromethanesulfonyl}naphthyl(5)

In an argon atmosphere, triethylamine (11.1 mmol) was added to a dichloromethane solution (25 mL) of Compound 4 (3.70 mmol), and the mixture was cooled to −78° C. Trifluoromethanesulfonic acid anhydride (11.1 mmol) was added dropwise, and the mixture was allowed to warm to room temperature, followed by stirring for 1 hour. Subsequently, the reaction mixture was poured into a saturated aqueous solution of ammonium chloride and the solution was extracted with dichloromethane. The dichloromethane solution was dried over anhydrous sodium sulfate and was concentrated under reduced pressure. After concentration, the resulting residue was subjected to a silica gel column chromatography and eluted with a mixed solvent of diethylether/hexane to give Compound 5 in a quantitative yield. Chemical data for the product are shown below.

$^1$H-NMR (400 MHz, CDCl$_3$) σ 8.33 (2H, s, Ar—H), 7.72 (2H, s, Ar—H), 7.47 (2H, dd, J=1.2.Hz, 8.4 Hz, Ar—H), 7.32 (2H, d, J=8.4 Hz, Ar—H), 2.05-1.87 (8H, m, CH$_2$CF$_2$), 1.35-1.24 (4H, m, SiCH$_2$), 1.05-1.01 (4H, m, SiCH$_2$), 0.66 (6H, s, SiCH$_3$), 0.64 (6H, s, SiCH$_3$), 0.43 (6H, s, SiCH$_3$), 0.41 (6H, s, SiCH$_3$).

Example 56

Synthesis of (R)-1,1'-bi-{4,6-bis(2-perfluorooctyl-ethyldimethylsilyl)-2-methoxycarbonyl}naphthyl (6)

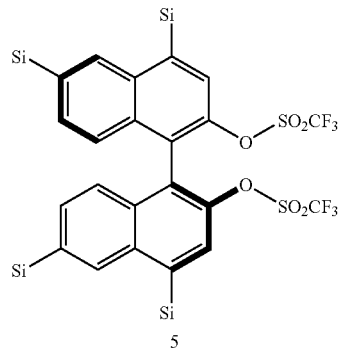

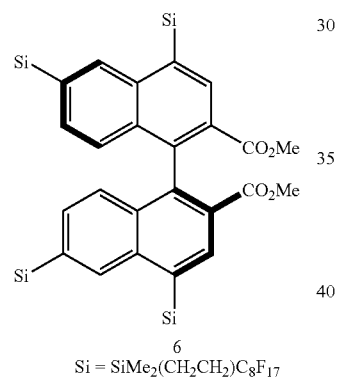

6
Si = SiMe$_2$(CH$_2$CH$_2$)C$_8$F$_{17}$

In an argon atmosphere, iPr$_2$Net (0.51 mL), MeOH (1.0 mL), and DMSO (2.0 mL) were added to a mixture containing Compound 5 (0.70 mmol), Pd(OAc)$_2$ (15 mol %), and dppp (16.5 mol %). While the reaction vessel was pressurized to 15 atm under CO atmosphere, the mixture was stirred at 100° C. for 24 hours. Subsequently, the reaction mixture was poured into water and the solution was extracted with ethyl acetate. The extract was dried over anhydrous sodium sulfate and was concentrated under reduced pressure. After concentration, the resulting residue was subjected to a silica gel column chromatography and eluted with a mixed solvent of diethylether/hexane to give Compound 6 in a yield of 70%. Chemical data for the product are shown below.

$^1$H-NMR (400 MHz, CDCl$_3$) σ 8.36 (2H, s, Ar—H), 8.29 (2H, s, Ar—H), 7.33 (2H, d, J=8.4 Hz, Ar—H), 7.23 (2H, d, J=8.4 Hz, Ar—H), 3.50 (6H, s, CO$_2$CH$_3$), 2.18-1.93 (8H, m, CH$_2$CF$_2$), 1.35-1.31 (4H, m, SiCH$_2$), 1.04-1.00 (4H, m, SiCH$_2$), 0.53 (12H, s, SiCH$_3$), 0.38 (12H, s, SiCH$_3$).

Example 57

Synthesis of (R)-1,1'-bi-{4,6-bis(2-perfluorooctyl-ethyldimethylsilyl)-2-hydroxymethyl)}naphthyl (7)

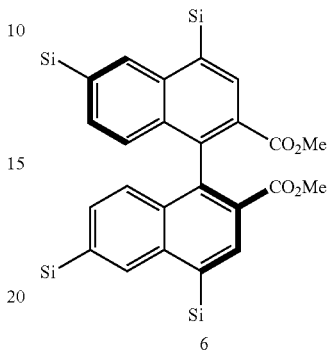

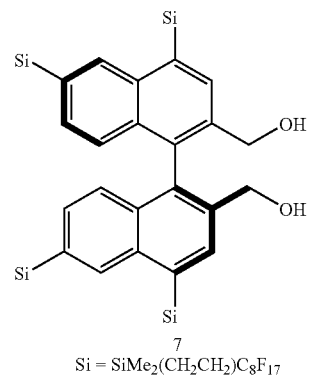

7
Si = SiMe$_2$(CH$_2$CH$_2$)C$_8$F$_{17}$

In an argon atmosphere, Compound 6 (0.44 mmol) was added to a tetrahydrofuran solution of LiAlH$_4$ (1.30 mmol) at 0° C., and the mixture was stirred for 1 hour. Subsequently, the reaction mixture was deactivated by sequentially adding MeOH and a saturated aqueous solution of ammonium chloride and the solution was extracted with diethylether. The extract was dried over anhydrous sodium sulfate and was concentrated under reduced pressure. The resulting residue was subjected to a silica gel column chromatography and eluted with a mixed solvent of diethylether/hexane to give Compound 7 in a quantitative yield. Chemical data for the product are shown below.

$^1$H-NMR (400 MHz, CDCl$_3$) σ 8.27 (2H, s, Ar—H), 7.90 (2H, s, Ar—H), 7.33 (2H, d, J=8.4 Hz, Ar—H), 7.10 (2H, d, J=8.4 Hz, Ar—H), 4.43 (2H, d, J=11.6 Hz, ArCH$_2$), 4.14 (2H, d, J=11.6 Hz, ArCH$_2$), 3.20 (2H, br s, OH), 2.16-1.98 (8H, m, CH$_2$CF$_2$), 1.34-1.29 (4H, m, SiCH$_2$), 1.06-1.01 (4H, m, SiCH$_2$), 0.63 (12H, s, SiCH$_3$), 0.37 (12H, s, SiCH$_3$).

Example 58

Synthesis of (R)-1,1'-bi-{4,6-bis(2-perfluorooctyl-ethyldimethylsilyl)-2-bromomethyl}naphthyl (8)

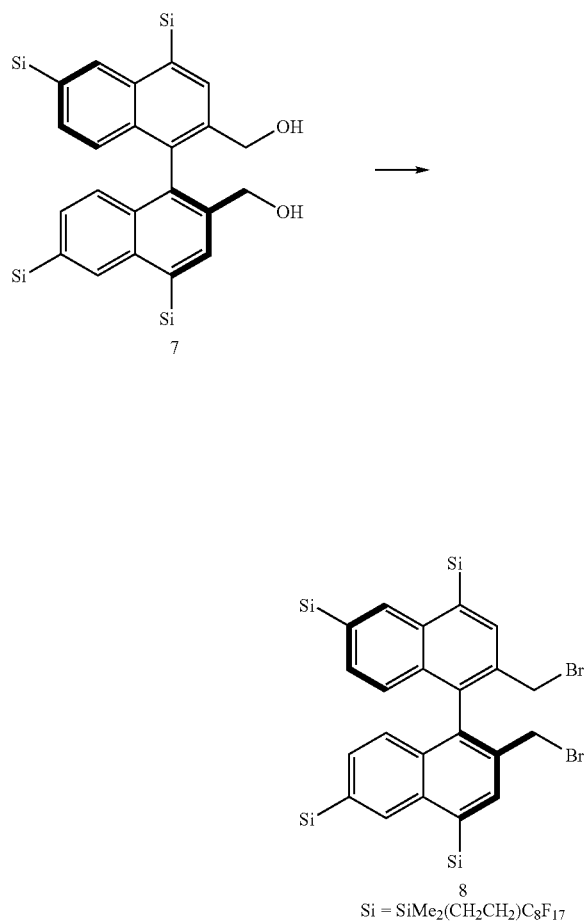

Triphenylphosphine (0.315 g, 1.2 mmol) and carbon tetrabromide (0.398 g, 1.2 mmol) were added to a tetrahydrofuran solution (10 mL) of Compound 7 (0.20 mmol), and the mixture was stirred at room temperature for 4 hours. After completion of the reaction, the reaction mixture was poured into water and was extracted with dichloromethane. The dichloromethane solution was dried over anhydrous sodium sulfate and was concentrated under reduced pressure. After concentration, the residue was subjected to a silica gel column chromatography and was eluted with a hexane solvent to give Compound 8 in a quantitative yield. Chemical data for the product are shown below.

$^1$H-NMR (400 MHz, CDCl$_3$) σ 8.25 (2H, s, Ar—H), 7.89 (2H, s, Ar—H), 7.35 (2H, dd, J=1.2 Hz, 8.4 Hz, Ar—H), 7.09 (2H, d, J=8.4 Hz, Ar—H), 4.23 (4H, s, ArCH$_2$), 2.17-1.97 (8H, m, CH$_2$CF$_2$), 1.34-1.25 (4H, m, SiCH$_2$), 1.04-1.00 (4H, m, SiCH$_2$), 0.64 (12H, s, SiCH$_3$), 0.38 (12H, s, SiCH$_3$).

Example 59

Synthesis of Spiro-bis-{(R)-1,1'-bi-[4,6-bis(2-perfluorooctylethyldimethylsilyl)]naphthyl-2,2'-dimethyl}ammonium bromide (9)

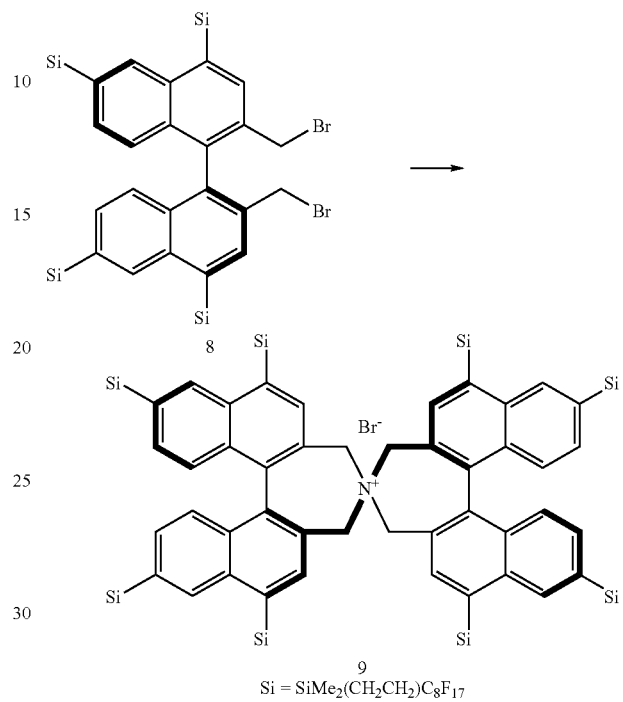

A 28% aqueous ammonia (0.77 mL, 12.6 mmol) and acetonitrile (5 mL) were added to Compounds 8 (3.15 mmol). The reaction vessel was sealed and the mixture was stirred for 24 hours while being refluxed. Subsequently, the reaction mixture was poured into water and the solution was extracted with dichloromethane. The extract was dried over anhydrous sodium sulfate and was concentrated under reduced pressure. After concentration, the resulting residue was subjected to a silica gel column chromatography and eluted with a mixed solvent of dichloromethane/methanol to give Compounds 9. Chemical data for the product are shown below.

$^1$H-NMR (400 MHz, CDCl$_3$) σ 8.41 (4H, s, Ar—H), 8.06 (4H, s, Ar—H), 7.39 (4H, d, J=8.4 Hz, Ar—H), 7.25 (4H, d, J=8.4 Hz, Ar—H), 4.48 (4H, d, J=13.6 Hz, ArCH$_2$), 4.26 (4H, d, J=13.6 Hz, ArCH$_2$), 2.20-1.98 (16H, m, CH$_2$CF$_2$), 1.44-1.40 (8H, m, SiCH$_2$), 1.07-1.03 (8H, m, SiCH$_2$), 0.84 (12H, s, SiCH$_3$), 0.79 (12H, s, SiCH$_3$), 0.60 (12H, s, SiCH$_3$), 0.43 (12H, s, SiCH$_3$).

Example 60

Asymmetric Alkylation Using Compound (9) as Optically Active Phase-transfer Catalyst, Recovery and Recycle of the Catalyst

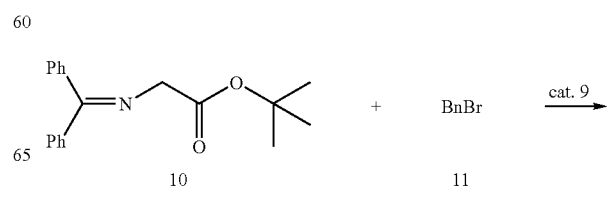

-continued

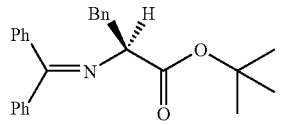

12

At 0° C. and in an argon atmosphere, benzyl bromide (11) (0.36 mmol) was added to a toluene solution (3.0 mL) of Compound (10) of the formula (12) (0.3 mmol) and Compound (9) of the formula (1) (0.009 mmol). A 50% aqueous solution of potassium hydroxide (1.0 mL) was added dropwise and the mixture was vigorously stirred for 96 hours at the same temperature. Subsequently, the mixture was diluted with water (3.0 mL) and toluene (3.0 mL), and Compound (9) was extracted from the diluted solution with FC-72 (perfluorohexane) (3.0 mL×3). The fluorous solvent was evaporated under reduced pressure and the remaining residue (quantitatively recovered for use as catalyst) was directly used in the subsequent reaction without further purification. The crude product, which was a mixed solution of toluene/water containing Compound (12) as a primary component, was extracted with ether. The organic phase was washed with saturated brine, dried over sodium sulfate, and concentrated under reduced pressure. The residue was subjected to a silica gel column chromatography to give the alkylated compound 12. The results are shown in Table 2.

Example 61

Using the catalyst recovered in Example 60, the same process was repeated in the same reaction scale, followed by the same post-process. The results are also shown in Table 2.

Example 62

Using the catalyst recovered again in Example 61, the same process was repeated in the same reaction scale, followed by the same post-process. The results are also shown in Table 2.

TABLE 2

|  | Catalyst 9 (Number of use) | Time (h) | Yield (%) | Optical Purity (%) |
|---|---|---|---|---|
| Example 60 | First time | 96 | 82 | 90 |
| Example 61 | Second time | 96 | 79 | 92 |
| Example 62 | Third time | 96 | 81 | 92 |

Examples 63 and 64

Asymmetric Alkylation Using Compound (9) as a Phase-transfer Catalyst

-continued

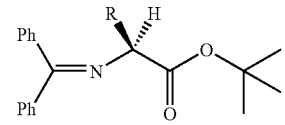

Using Compound (9) as a catalyst, asymmetric alkylation was carried out in the same manner as in Example 60, except that a substrate shown as R—Y in Table 3 was used. The results are together shown in Table 3.

TABLE 3

|  | R-Y | Time (h) | Yield (%) | Optical Purity (%) |
|---|---|---|---|---|
| Example 63 | $CH_2$=$CHCH_2Br$ | 142 | 80 | 84 |
| Example 64 | HC≡$CCH_2Br$ | 140 | 81 | 90 |

The optical purity of the reaction products was determined according to the technique described in *J. Am. Chem. Soc.* 1999, Vol. 121, No. 27, 6519-6520.

The invention claimed is:

1. An optically active quaternary ammonium salt, represented by the following formula (1a):

(1a)

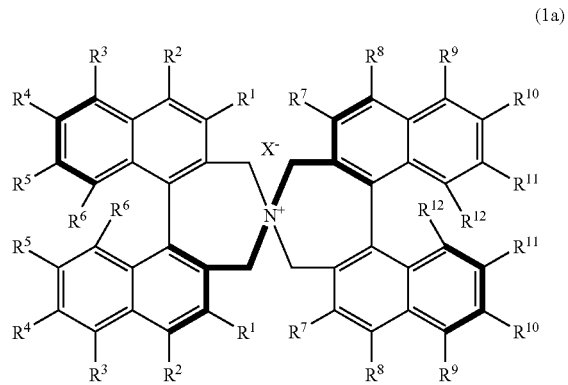

[wherein $R^1$, $R^2$, $R^3$, $R^4$, $R^5$, $R^6$, $R^7$, $R^8$, $R^9$, $R^{10}$, $R^{11}$, and $R^{12}$ are each independently a hydrogen atom, a methyl group, an ethyl group, a straight, branched or cyclic alkyl group having 3 to 18 carbon atoms, a straight, branched or cyclic heteroalkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 35 carbon atoms, or a heteroaralkyl group having 5 to 35 carbon atoms;

with the proviso that at least one of $R^1$, $R^2$, $R^3$, $R^4$, $R^5$, $R^6$, $R^7$, $R^8$, $R^9$, $R^{10}$, $R^{11}$, and $R^{12}$ is a substituent represented by the following formula (2a):

(2a)

(wherein $R^{13}$, $R^{14}$, and $R^{15}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms);

$X^-$ is a fluorine ion, a chloride ion, a bromide ion, an iodide ion, a p-toluenesulfonic acid ion, a hydroxide ion, a thiocyanate ion, a hydrogen sulfate ion, a perchioric acid ion, or a hexafluorophosphoric acid ion; and the two binapbthyl moieties each have a chiral axis so that the absolute configurations of the two binaphthyl moieties are (R, R) or (S, S)].

2. The optically active quaternary ammonium salt according to claim 1, wherein $R^1$ and $R^7$, $R^3$ and $R^9$, $R^4$ and $R^{10}$, $R^5$ and $R^{11}$, and $R^6$ and $R^{12}$ in the formula (1a) are in each case identical to one another; $R^2$ and $R^8$ are identical to one another and are each represented by the formula (2a); and $X^-$ is a fluorine ion, a chloride ion, a bromide ion, an iodide ion, a p-toluenesulfonic acid ion, or a hydroxide ion.

3. The optically active quaternary ammonium salt according to claim 1, wherein $R^1$, $R^3$, $R^5$, $R^6$, $R^7$, $R^9$, $R^{11}$, and $R^{12}$ in the formula (1a) are each independently a hydrogen atom; $R^2$, $R^4$, $R^8$, and $R^{10}$ are identical to one another and are each represented by the formula (2a); and $X^-$ is a chloride ion, a bromide ion, an iodide ion, or a p-toluenesulfonic acid ion.

4. The optically active quaternary ammonium salt according to claim 1, wherein in the formula (1a), $R^1$ and $R^7$, $R^3$ and $R^9$, $R^4$ and $R^{10}$, $R^5$ and $R^{11}$, and $R^6$ and $R^{12}$ are in each case identical to one another, $R^2$ and $R^8$ are identical to one another and are each represented by the formula (2a), and $X^-$ is a bromide ion; and $R^{13}$, $R^{14}$ and $R^{15}$ in the formula (2a) are each independently a substituent selected from the group consisting of a methyl group, an ethyl group, an n-propyl group, an isopropyl group, an n-butyl group, an isobutyl group, a sec-butyl group, a tert-butyl group, an n-octyl group, end a phenyl group.

5. An optically active quaternary ammonium salt represented by the following formula (1b):

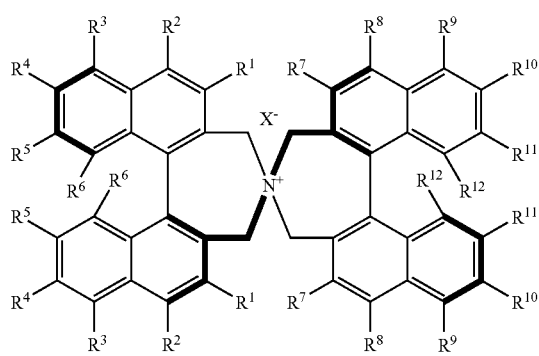

(1b)

[wherein $R^1$, $R^2$, $R^3$, $R^4$, $R^5$, $R^6$, $R^7$, $R^8$, $R^9$, $R^{10}$, $R^{11}$, and $R^{12}$ are each independently a hydrogen atom, a halogen atom, a methyl group that may or may not be substituted with fluorine, an ethyl group that may or may not be substituted With fluorine, a straight branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an alkynyl group that has 5 to 35 carbon atoms and may or may not be substituted with fluorine, or a heteroaralkyl group tat has 5 to 35 carbon atoms and may or may not be substituted with fluorine;

with the proviso that at least one of $R^1$, $R^2$, $R^3$, $R^4$, $R^5$, $R^6$, $R^7$, $R^8$, $R^9$, $R^{10}$, $R^{11}$, and $R^{12}$ is a substituent represented by the following formula (2b):

$Pf(CH_2)_n—$ (2b)

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.), and/or by the following formula (2c):

(2c)

(wherein Pf and n are as defined in the formula (2b) above, $R^{13}$ and $R^{14}$ are each independently a methyl group, an ethyl group, a vinyl group, a straight, branched or cyclic alkyl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an aralkyl group having 5 to 25 carbon atoms, or a heteroaralkyl group having 5 to 25 carbon atoms.);

$X^-$ is a fluoride ion, a chloride ion, a bromide ion, an iodide ion, a p-toluenesulfonic acid ion, a hydroxide ion, a thiocyanate ion, a hydrogen sulfate ion, a perchloric acid ion, or a hexafluorophosphoric acid ion; and the two binaphthyl moieties each have a chiral axis so that the absolute configurations of the two binaphthyl moieties are (R, R) or (S, S)].

6. The optically active quaternary ammonium salt according to claim 5, wherein $R^1$ and $R^7$, $R^3$ and $R^9$, $R^4$ and $R^{10}$, $R^5$ and $R^{11}$, $R^6$ and $R^{12}$ in the formula (1b) are in each case identical to one another; $R^2$ and $R^8$ are identical to one another and are each represented by the formula (2a); and $X^-$ is a fluorine ion, a chloride ion, a bromide ion, an iodide ion, a p-toluenesulfonic acid ion, a thiocyanate ion, a hydrogen sulfate ion, or a hydroxide ion.

7. The optically active quaternary ammonium salt according to claim 5, wherein $R^1$, $R^3$, $R^5$, $R^6$, $R^7$, $R^9$, $R^{11}$, and $R^{12}$ in the formula (1b) are each independently a hydrogen atom; $R^2$, $R^4$, $R^8$, and $R^{10}$ are identical to one another and are each represented by the formula (2c); and $X^-$ is a chloride ion, a bromide ion, an iodide ion, or a p-toluenesulfonic acid ion.

8. The optically active quaternary ammonium salt according to claim 5, wherein in the formula (1b), $R^1$ and $R^7$, $R^3$ and $R^9$, $R^4$ and $R^{10}$, $R^5$ and $R^{11}$, and $R^6$ and $R^{12}$ are in each case identical to one another, and $X^-$ is a bromide ion; and in the formula (2c), n is 2, $R^{13}$ and $R^{14}$ are each a methyl group, and Pf is an n-octyl group having all the hydrogen atoms substituted with fluorine atoms.

9. A method for producing the optically active quaternary ammonium salt according to claim 1 or claim 5 represented by the formula (1a) or (1b) wherein $R^1$, $R^2$, $R^3$, $R^4$, $R^5$, and $R^6$ are each independently a hydrogen atom, a methyl group, an ethyl group, a straight, branched or cyclic alkyl group having 3 to 18 carbon atoms, a straight, branched or cyclic heteroalkvl group having 3 to 18 carbon atoms, a straight, branched or cyclic alkenyl group having 3 to 18 carbon atoms, a straight, branched or cyclic alkynyl group having 3 to 18 carbon atoms, an alkoxyl group having 1 to 18 carbon atoms, an aryl group having 5 to 20 carbon atoms, an alkoxyl group having 5 to 35 carbon atoms, or a heteroaralkyl group having 5 to 35 carbon atoms and in which $X^-$ is a chloride ion, a bromide ion, a iodide ion, or a p-toluenesulfonic acid ion, characterized in that the optically active binaphthyl compound represented by the formula (3a)

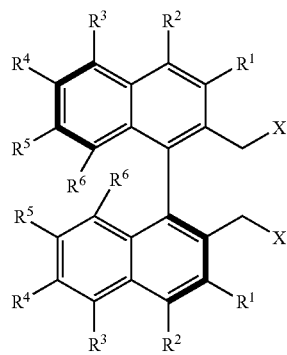

(3a)

or (3b)

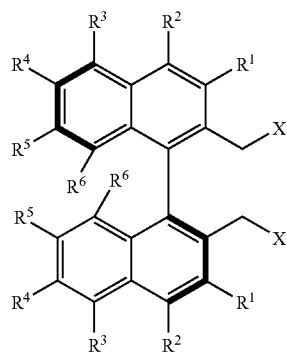

(3b)

is reacted with ammonia.

10. A method for recovering an optically active quaternary ammonium salt, wherein an organic solvent, water, a mixed solvent of an organic solvent and water, and/or an organic solvent with hydrogen atoms substituted with fluorine atoms are/is used to separate the optically active quaternary ammonium salt represented by the following formula (1b):

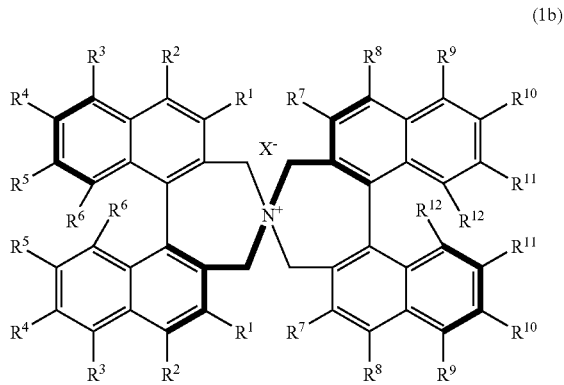

(1b)

[wherein $R^1$, $R^2$, $R^3$, $R^4$, $R^5$, $R^6$, $R^7$, $R^8$, $R^9$, $R^{10}$, $R^{11}$, and $R^{12}$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight, branched or cyclic alkenyl group that has 3 to 18 carbon atoms and may or may not be substituted with fluorine, a straight, branched or cyclic alkynyl group that has 3 to 18 carbon atoms and may or may not be substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substituted with fluorine;

with the proviso that at least one of $R^1$, $R^2$, $R^3$, $R^4$, $R^5$, $R^6$, $R^7$, $R^8$, $R^9$, $R^{10}$, $R^{11}$, and $R^{12}$ is a substituent represented by the following formula (2b):

$Pf(CH_2)_n—$ (2b)

(wherein Pf is a straight, branch or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.) from a product containing the ammonium salt.

11. A method for recovering the optically active quaternary ammonium salt, represented by the following formula (1b):

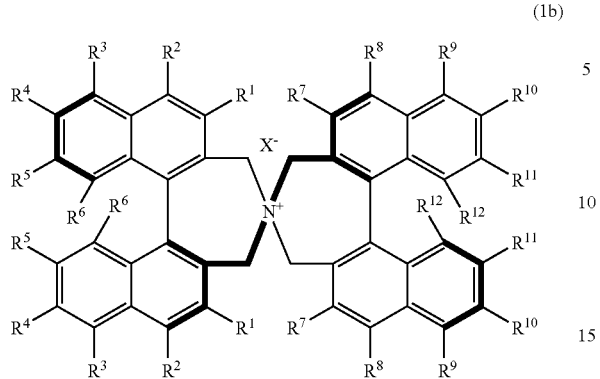

(1b)

[wherein $R^1$, $R^2$, $R^3$, $R^4$, $R^5$, $R^6$, $R^7$, $R^8$, $R^9$, $R^{10}$, $R^{11}$, and $R^{12}$ are each independently a hydrogen atom, a halogen atom, a methyl group that may or may not be substituted with fluorine, an ethyl group that may or may not be substituted with fluorine, a straight, branched or cyclic alkyl group that has 3 to 18 carbon atoms and may or may not be substituted with fluorine, a straight, branched or cyclic heteroalkyl group that has 3 to 18 carbon atoms and may or may not be substituted with fluorine, a straight branched or cyclic alkenyl group that has 3 to 18 carbon atoms and may or may not be substituted with fluorine, a straight, branched or cyclic alkynyl group that has 3 to 18 carbon atoms and may or may not her substituted with fluorine, an alkoxyl group that has 1 to 18 carbon atoms and may or may not be substituted with fluorine, an aryl group that has 5 to 20 carbon atoms and may or may not be substituted with fluorine, an aralkyl group that has 5 to 35 carbon atoms and may or may not be substituted with fluorine, or a heteroaralkyl group that has 5 to 35 carbon atoms and may or may not be substitute with fluorine;

with the proviso that at least one of $R^1$, $R^2$, $R^3$, $R^4$, $R^5$, $R^6$, $R^7$, $R^8$, $R^9$, $R^{10}$, $R^{11}$, and $R^{12}$ is a substituent represented by the following formula (2b):

(2b)

(wherein Pf is a straight, branched or cyclic alkyl group that has 2 to 18 carbon atoms and has all the hydrogen atoms substituted with fluorine atoms, a straight, branched or cyclic alkenyl group that has 3 to 18 carbon atoms and has all the hydrogen atoms substituted with fluorine atoms, a straight, branched or cyclic alkynyl group that has 3 to 18 carbon atoms and has all the hydrogen atoms substituted with fluorine atoms, an aryl group that has 5 to 20 carbon atoms and has all the hydrogen atoms substituted with fluorine atoms, an aralkyl group that has 5 to 25 carbon atoms and has all the hydrogen atoms substituted with fluorine atoms, or a heteroaralkyl group that has 5 to 25 carbon atoms and has all the hydrogen atoms substituted with fluorine atoms, and n is an integer from 0 to 4.) wherein following the production of the compound of the formula (14)

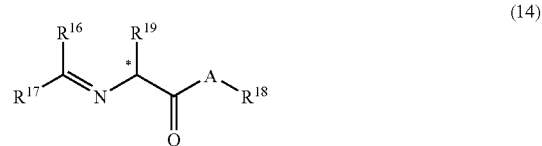

(14)

wherein $R^{16}$ and $R^{17}$ are each independently a hydrogen atom or an aryl group that has 5 to 10 carbon atoms and may or may not be substituted with halogen, with the proviso that $R^{16}$ and $R^{17}$ are not a hydrogen atom at the same time;

A is an oxygen atom or a nitrogen atom having a single hydrogen atom bound thereto; and $R^{19}$ is a straight, branched or cyclic alkyl group having 1 to 10 carbon atoms, a straight, branched or cyclic alkenyl group having 3 to 10 carbon atoms, a straight branched or cyclic alkynyl group having 3 to 10 carbon atoms, or an aralkyl group that has 5 to 25 carbon atoms and may or may not have its nucleus substituted with 1 to 15 hydrogen atoms;

by the method which is carried out in the presence of the optically active quaternary ammonium salt of the formula (1b), the ammonium salt is separated from the reaction mixture containing the optically active quaternary ammonium salt by using an organic solvent, water, a mixed solvent of an organic solvent and water, and/or an organic solvent with hydrogen atoms substituted with fluorine atoms.

12. The method according to claim 11, wherein hexane with its hydrogen atoms substituted with fluorine atoms is used as the fluorine-substituted organic solvent.

\* \* \* \* \*